United States Patent
Yacoubian

(10) Patent No.: US 7,397,596 B2
(45) Date of Patent: Jul. 8, 2008

(54) SURFACE AND SUBSURFACE DETECTION SENSOR

(75) Inventor: Araz Yacoubian, Carlsbad, CA (US)

(73) Assignee: Ler Technologies, Inc., Encinitas, CA (US)

( * ) Notice: Subject to any disclaimer, the term of this patent is extended or adjusted under 35 U.S.C. 154(b) by 146 days.

(21) Appl. No.: 11/437,776

(22) Filed: May 18, 2006

(65) Prior Publication Data

US 2006/0215175 A1   Sep. 28, 2006

Related U.S. Application Data

(63) Continuation-in-part of application No. 10/902,437, filed on Jul. 28, 2004.

(60) Provisional application No. 60/746,599, filed on May 5, 2006, provisional application No. 60/748,083, filed on Dec. 6, 2005, provisional application No. 60/682,315, filed on May 18, 2005, provisional application No. 60/682,127, filed on May 18, 2005, provisional application No. 60/682,299, filed on May 18, 2005.

(51) Int. Cl.
    *G02B 26/00* (2006.01)
(52) U.S. Cl. .................................... 359/290
(58) Field of Classification Search .............. 359/247, 359/290, 302; 356/432, 502; 73/655, 657
    See application file for complete search history.

(56) References Cited

U.S. PATENT DOCUMENTS

| | | | |
|---|---|---|---|
| 4,448,525 A | 5/1984 | Mikoshiba et al. | |
| 4,572,949 A * | 2/1986 | Bowers et al. | 250/227.27 |
| 4,874,251 A | 10/1989 | Thomas et al. | |
| 5,083,869 A | 1/1992 | Nakata et al. | |
| 5,136,172 A | 8/1992 | Nakata et al. | |
| 5,706,094 A | 1/1998 | Maris | |
| 6,008,906 A | 12/1999 | Maris | |
| 6,211,961 B1 | 4/2001 | Maris | |
| 6,216,540 B1 | 4/2001 | Nelson et al. | |
| 6,268,916 B1 | 7/2001 | Lee et al. | |
| 6,411,390 B1 | 6/2002 | Nikoonahad et al. | |
| 6,504,618 B2 | 1/2003 | Morath et al. | |
| 6,552,803 B1 | 4/2003 | Wang et al. | |
| 6,786,099 B2 | 9/2004 | Janik | |
| 6,806,951 B2 | 10/2004 | Wack et al. | |
| 6,818,459 B2 | 11/2004 | Wack et al. | |
| 6,829,559 B2 | 12/2004 | Bullman et al. | |
| 6,891,610 B2 | 5/2005 | Nikoonahad et al. | |

(Continued)

OTHER PUBLICATIONS

R.M. Silver, et al., The Limits of Image-Based Oprical Metrology, Proc. SPIE vol. 6152, 61520Z, Metrology, Inspection, and Process Control for Microlithography XX; Chas N. Archie; Ed., Mar. 2006.

(Continued)

*Primary Examiner*—Ricky L Mack
*Assistant Examiner*—William C Choi
(74) *Attorney, Agent, or Firm*—Koestner Bertani LLP; Ken J. Koestner

(57) ABSTRACT

A sensor comprises an optical modulator that generates a modulation signal, an interferometer that mixes an acoustic signal evoked by a pulsed laser with the modulation signal to down-convert the acoustic signal to lower frequencies, and a photodetector that detects the down-converted signal.

61 Claims, 36 Drawing Sheets

U.S. PATENT DOCUMENTS

| | | |
|---|---|---|
| 6,891,627 B1 | 5/2005 | Levy et al. |
| 6,917,419 B2 | 7/2005 | Fielden et al. |
| 6,919,957 B2 | 7/2005 | Nikoonahad et al. |
| 6,937,340 B2 | 8/2005 | Roudil et al. |
| 6,946,394 B2 | 9/2005 | Fielden et al. |
| 6,950,196 B2 | 9/2005 | Fielden et al. |
| 6,979,292 B2 | 12/2005 | Kanayama et al. |
| 7,006,221 B2 | 2/2006 | Wolf et al. |
| 7,006,235 B2 | 2/2006 | Levy et al. |

OTHER PUBLICATIONS

R.M. Silver et al., High-Resolution Optical Metrology, Proc. SPIE vol. 5752, p. 67-79, Metrology, Inspection, and Process Control for Microlithography XIX; Richard M. Sllver; Ed., May 2005.

\* cited by examiner

TABLE I

| Description | Spot size | Units | Measurement Time (seconds) | Measurement Time (minutes) | Wafers per hour | Notes |
|---|---|---|---|---|---|---|
| Single Scan diameter | 0.5 | um | 2.00E-07 | | | (5 MHz detection, or 0.1 microseconds) |
| Single scan area | 0.25 | um^2 | | | | |
| | | | | | | Number of measurements for finer resolution: 100 |
| High-Res. Scan diameter | 0.05 | um | 2.00E-05 | | | |
| High-Res. Scan area | 0.0025 | | | | | |
| Total scan area (1000x1000) | 250000 | um^2 | | | | Each measurement |
| | | | | | | |
| Square centimeter area: | 100000000 | um^2 | | | | |
| Scans per cm^2 | 400 | | 8.00E-03 | | | (assuming no other delays) |
| Scans per cm^2 | 400 | | 0.40 | | | (assuming 1 ms delay per movement) |
| | | | | | | |
| 300 cm Wafer Area | 70683750000 | | | | | |
| Scans per 300 cm wafer | 282735 | | 5.65E+00 | 0.09 | 636.64 | (assuming no other delays) |
| Scans per 300 cm wafer | 282735 | | 2.83E+02 | 4.71 | 12.73 | (assuming 1 ms delay per movement) |
| Full wafer scan with 25 parallel heads at 1ms/movement | | | | 0.19 min./wafer | | (no need for multiple heads |
| Single wafer scan: | Wafers per hour w/25 heads | | | 318.32 wafers/hr | | |

FIG. 9B

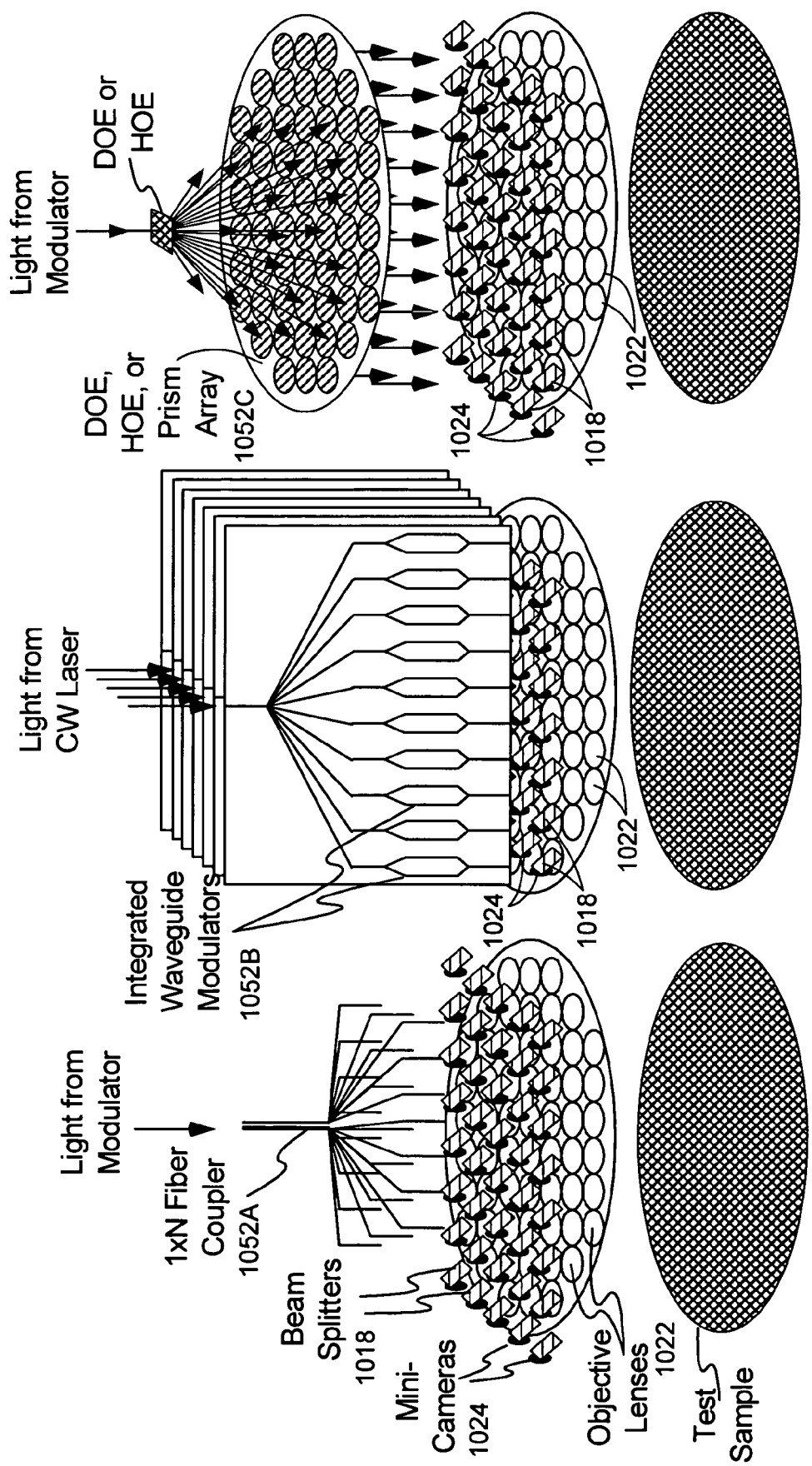

Objective Lenses 1122A

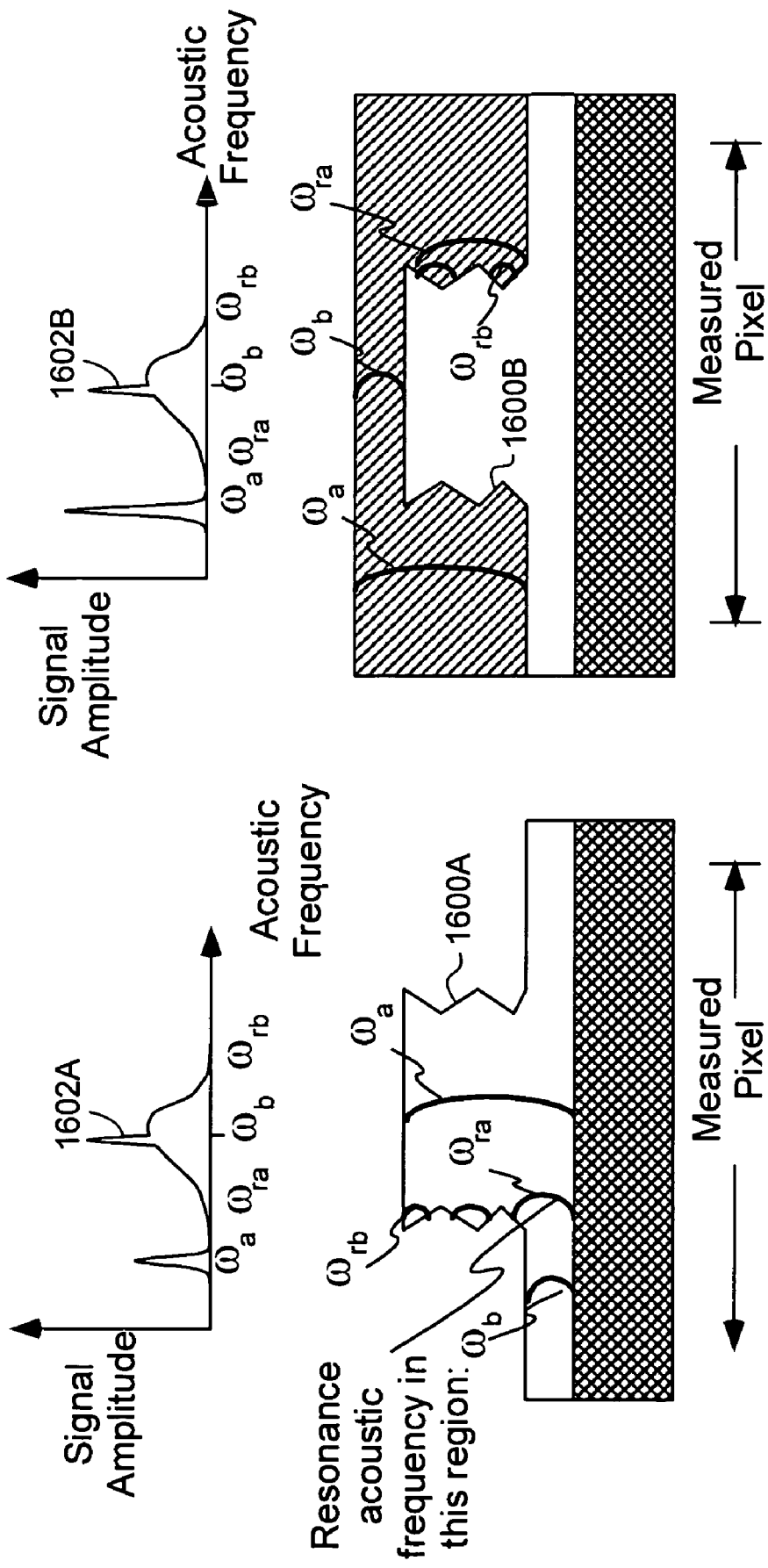

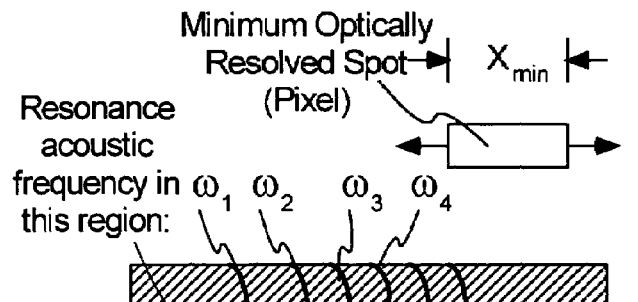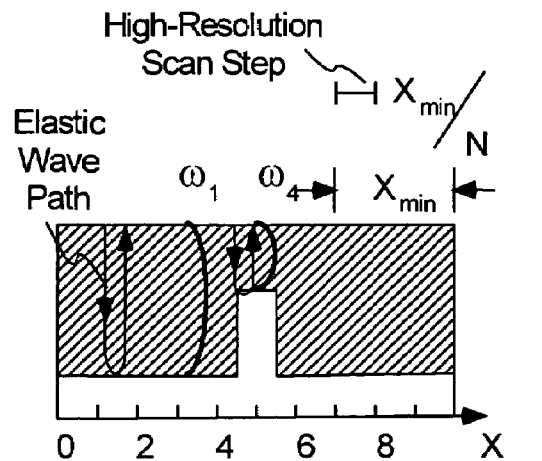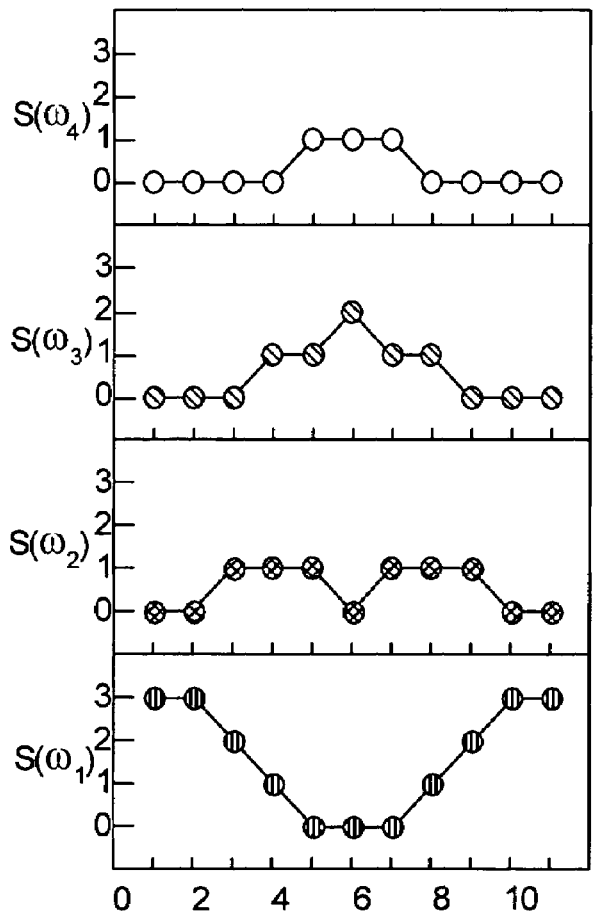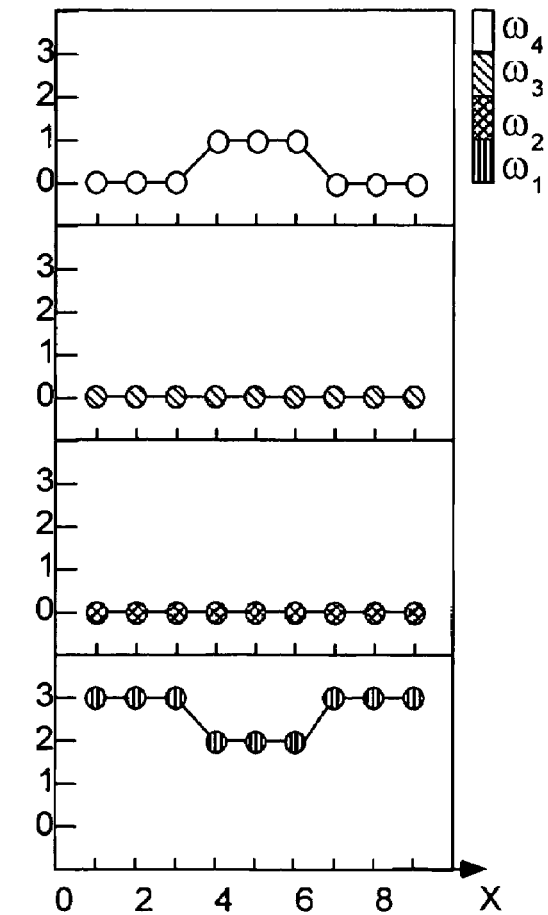
FIG. 17A    FIG. 17B

SURFACE AND SUBSURFACE DETECTION SENSOR

This application claims the benefit of priority to and incorporates herein by reference in its entirety for all purposes, U.S. Provisional Patent Application No. 60/682,315 entitled "HIGH-RESOLUTION SURFACE AND SUBSURFACE DETECTION METHOD," by Araz Yacoubian filed on May 18, 2005; U.S. Provisional Patent Application No. 60/682,127 entitled "SURFACE AND SUBSURFACE DETECTION METHOD WITH DIRECT LIGHT MODULATION," by Araz Yacoubian filed on May 18, 2005; U.S. Provisional Patent Application No. 60/682,299 entitled "HIGH-RESOLUTION PHASE SENSITIVE SURFACE AND SUBSURFACE DETECTION METHOD," by Araz Yacoubian filed May 18, 2005; U.S. Provisional Patent Application No. 60/748,083 entitled "High Frequency Modulation Using Multiple Cascaded or Parallel Modulators and Lasers," by Araz Yacoubian filed Dec. 6, 2005; and U.S. Provisional Patent Application No. 60/746,599 entitled "HIGH-RESOLUTION SURFACE AND SUBSURFACE DETECTION METHOD," by Araz Yacoubian filed May 5, 2006. This application is a continuation-in-part and incorporates herein by reference in its entirety for all purposes, U.S. patent application Ser. No.: 10/902,437 entitled "ELECTRO-OPTIC SENSOR," by Araz Yacoubian filed Jul. 28, 2004

BACKGROUND OF THE INVENTION

Technical and economic factors continue to drive the evolution of semiconductor processing equipment. The semiconductor industry demands fabrication machines with a capability to process semiconductor wafers at high speed with substantial uniformity and reliability. Integrated circuit fabrication commonly involves numerous process steps with fabrication machinery processing semiconductor wafers at high speed to create structural features with high precision. Measurements are commonly made between process steps to verify features are within tolerances demanding a capability to perform non-destructive inspection and analysis of semiconductor wafers.

Optical metrology is a highly useful technique for non-destructive analysis. Examples of optical metrology include ellipsometry, reflectometry, scatterometry, and others. Ellipsometry involves analysis of changes in polarization state of probe illumination. Reflectometry relates to analysis of changes in illumination intensity. Scatterometry is analysis of diffraction in response to illumination that creates optical scattering of a probe beam. As semiconductor geometries constantly evolve to smaller integrated circuit critical dimensions, optical interrogation wavelengths decrease.

Because the semiconductor fabrication process takes place in a strictly controlled environment, the impact of non-destructive analysis equipment and techniques on the environment is desired to be minimal. Accordingly, desired characteristics of analysis equipment include aspects such as small size, capability to remain conveniently located with respect to process chambers and equipment, capability to perform measurements and analysis without contacting the semiconductor wafers, and capability of remote control.

SUMMARY OF THE INVENTION

In an illustrative embodiment, a sensor comprises an optical modulator that generates a modulation signal, an interferometer that mixes an acoustic signal evoked by a pulsed laser with the modulation signal to down-convert the acoustic signal to lower frequencies, and a photo detector that detects the down-converted signal.

BRIEF DESCRIPTION OF THE DRAWINGS

Embodiments of the invention relating to both structure and method of operation, may best be understood by referring to the following description and accompanying drawings:

FIGS. 9A and 9B are respectively, a schematic pictorial and block diagram showing an embodiment of an interferometer that enables analysis and enhancement of scan speed, and a Table showing results of an example scan speed enhancement implementation;

FIGS. 10A, 10B, and 10C are schematic pictorial diagrams illustrating embodiments of interferometer structures that can be used to interrogate a large area at a very rapid rate;

FIGS. 16A and 16B are cross-sectional pictorial views and corresponding spectral graphs depicting line-edge roughness detection;

FIGS. 17A and 17B are cross-sectional pictorial views and corresponding spectral graphs illustrating a technique for high-resolution detection by moving a sample or the optical system at step sizes finer than the optical resolution limit;

DETAILED DESCRIPTION OF THE EMBODIMENTS

Sensors in various configurations and arrangements use optics, integrated optics, optical waveguides, interferometer, laser ultrasonics, acoustics, optical modulators, fiber-optics, and bulk-optic interferometers to perform various measurements and analysis, for example in testing of semiconductor materials, nondestructive evaluation, imaging, metrology, line edge roughness, phase measurement. In some applications, the various sensors detect pulsed laser-induced high-frequency acoustic resonance in a multi-layer material. The sensor down-converts high-frequency (GHz) acoustic signals to low-frequency (kHz) detectable signals. The resulting measurement may be either a single point defect signature or a two-dimensional (2D) acoustic "image" indicating subsurface defects. Defect examples include delamination, thickness variation, cracks, inclusions, and damaged micro- or nano-structure. Various architectures may be used for single point measurements and two-dimensional (2D) measurements, acquired in normal incidence and arbitrary angle of incidence measurements. The appended drawings depict several examples of suitable sensor structures.

Various sensor architectures are described which are adapted for surface and subsurface testing and analysis of materials. In some embodiments and applications, high-resolution sensor structures and operating methods increase the detection resolution beyond the optical limit. Applications of high resolution sensors can include, but are not limited to, defect detection, surface and subsurface interrogation, metrology, non-destructive evaluation of semiconductor wafers and integrated circuits (IC) either after processing or during processing (in-situ), and interrogation of defects in metals and various materials. In some embodiments and applications, scan speed of the sensing methodology is described along with techniques for enhancing scan speed. Sensors are depicted that are applicable to metrology. Some sensors and sensing methods may include various acoustic excitation methods. Some applications and embodiments use polarization optics to enhance signal-to-noise ratio and for better control of light.

In some configurations, the sensors and techniques can be extended to phase sensitive measurements, enabling acquisition of additional information that reveals the location of the object and yields higher-than-optical resolution.

Some arrangements include sensor structures and techniques for generating acoustic excitation using directly modulated laser beam.

Configurations are also described which include sensor structures and techniques that use multiple modulators to modulate light at higher frequency than using a single modulator.

Figure 1A:
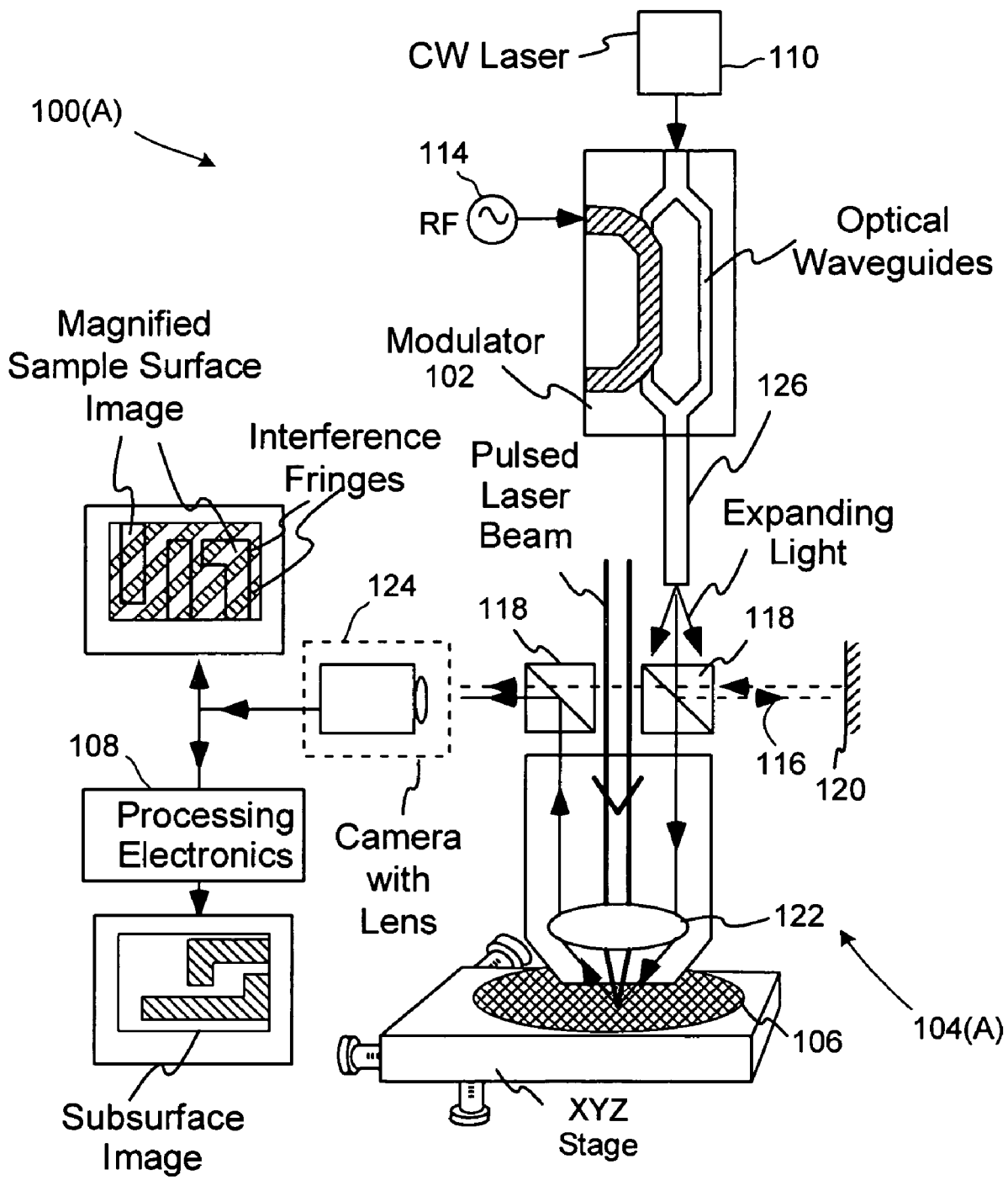
FIGS. 1A and 1B are schematic combined pictorial and block diagrams depicting embodiments of sensor architectures adapted for surface and subsurface detection.
Figure 1B:
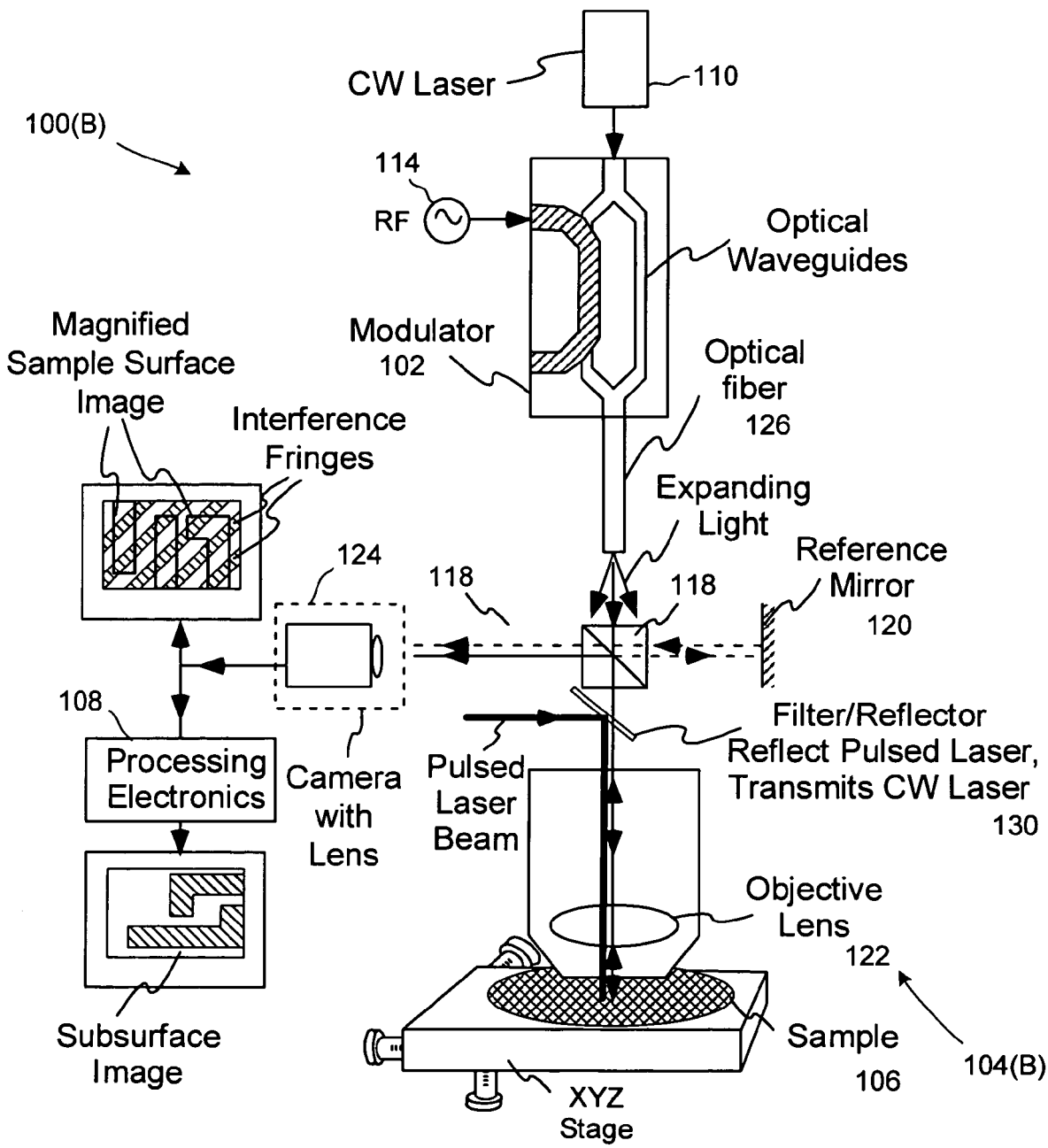

Referring to FIGS. 1A and 1B, schematic combined pictorial and block diagrams depict embodiments of sensor architectures adapted for surface and subsurface detection. A cascaded modulator/interferometer sensor architecture 100 comprises a light modulator 102 followed by an interferometer 104 and detects pulsed laser-induced high-frequency acoustic resonance in a single or a multi-layer material 106. The sensor 100 down-converts high-frequency, for example gigahertz (GHz) acoustic signals to low-frequency such as kilohertz (kHz) to megahertz (MHz) detectable signals. The sensor 100 can produce either a single point defect signature or a two-dimensional (2D) acoustic "image" capable of indicating subsurface defects such as delamination, thickness variation, cracks, inclusions, voids, damaged micro- or nano-structure, and surface and sub-surface features. Emphasis can be placed on obtaining a subsurface image, rather than a single point measurement, although the structures and methods are similarly applicable to single point scan.

The illustrative sensors 100A and 100B have cascaded interferometric architectures that enable detection and analysis of subsurface patterns and defects. Solid and dashed lines in FIGS. 1A and 1B illustrate reference and object light paths (optic axis), respectively. Processing electronics 108 can perform operations including band pass filtering, and image subtraction and image processing algorithms. A continuous wave (CW) laser 110 generates a CW laser beam that is passed to the modulator 102 which is modulated and passed to the interferometer 104 via a beam splitter 118. The modulator 102 is modulated via modulation signal from a radio frequency signal (RF) generator 114. Modulator 102 can be an integrated Mach-Zehnder modulator with electrodes shown in gray and waveguides depicted as clear, but can also be direct modulated laser, an electro-absorption modulator, or any other suitable component capable of modulating the CW laser light. Prisms and optical components 116 can be inserted between the beam splitter 118 and a reference mirror 120 to attain optical delay at a short distance. Illustrative bulk interferometers 104 are shown as a Mach-Zehnder interferometer 104A in FIG. 1A and a Michelson interferometer 104B in FIG. 1B. The Michelson interferometer 104B includes a filter/reflector 130 which reflects the pulsed laser signal and transmits the continuous wave laser.

The interferometer 104 has an objective lens 122 which has at least two purposes. First, the objective lens 122 images the sample surface 106 onto a multiple-dimensional photodetector 124, such as a camera. The image interferes with the reference beam, thereby creating an interference pattern. Second, the objective lens 122 focuses the pulsed laser onto the substrate 106. The pulsed laser beam excites elastic waves in the material which travel inward towards the sample 106 and also along the surface of the sample 106. The elastic waves reflect back from various interfaces, subsurface structures, and defects to the surface, and cause physical changes near the surface. Examples of the physical changes are small amplitude vibrations in the surface of the sample, or refractive index changes near the surface. The physical changes cause a change in the phase of the probe (continuous wave, CW) laser beam.

In a typical operation, the sample 106 on the XYZ stage is stepped or scanned in a two or three-dimensional field by a stepper or scanner.

Image signals can be passed from the camera 124 to a display that shows a magnified sample image and an interference pattern, and also can be passed to the processing electronics 108 and to a second display that shows a subsurface image.

The probe beam reflects from the sample surface (object beam) or from layer interfaces close to surface of the sample 106, and is reflected back and directed to the camera 124. The object beam interferes with the reference beam, and interference fringes are produced within the viewing area of the objective lens 122. For a phase difference between the object and reference beam, the fringes shift, or in case of single large fringe, the fringe changes from brighter to darker or vise versa. Physical changes that occur due to the pulsed laser therefore shift the fringes. Changes occur in the gigahertz (GHz) time scale if the features of interest have nanometer length scale, changes that are too fast to be captured even by a high-speed camera, resulting in excessively high detection noise. Accordingly, the illustrative sensor 100 down converts the signal to lower frequencies. With a modulator placed before the bulk interferometer 104 as shown in FIGS. 1A and 1B, or for a directly modulated laser such as a high-speed laser diode, the modulated signal mixes with the elastic wave-generated signal (an acoustic signal), and produces sum and difference frequencies. By adjusting modulation to a particular frequency, specifically if the modulation frequency is close to the acoustic resonance frequency, fringes are observed that change at much lower frequency than the acoustic signal due to the difference frequency generation, specifically frequency down-conversion.

For example, if a subsurface structure within part of the sample produces acoustic resonance at 50 GHz and the modulator is modulated at 50.005 GHz, then in the pertinent region, the fringes shift at the rate of 5 MHz, which is much easier to detect than at 50 GHz. If the modulator frequency is scanned within a range, and if various measurements are taken, the measurements yield the spatially varying acoustic spectrum of the sample, thus indicating presence of subsurface features and defects, and size, depth, location, shape, and type. The type of a defect can be obtained by observing the spectrum shape.

In the illustrative architectures depicted in FIGS. 1A and 1B, the modulator 102 is terminated with a bare fiber. At the end of the fiber, light expands, eliminating a need for any additional optics following the modulator 102. If the modulator is a direct laser modulator, then expanding optics such as a positive or negative lens can be used to diverge light. The objective lens 122 can be set to focus the pulsed laser beam, which is a collimated beam or a direct laser beam with low divergence angle. The focusing mechanism of the objective lens 122 concentrates the pulsed laser beam to a small spot, thus creating sufficiently high energy pulse to generate a detectable acoustic signal. The probe beam, for example the CW beam from the modulator, is not collimated, and therefore illuminates a larger part of the sample and yields an interferometric image of the sample 106.

FIG. 1A shows a Mach-Zehnder bulk interferometer 104A and FIG. 1B illustrates a Michelson interferometer 104B following the modulator 102. The modulator 102 can be an electro-optic modulator, a direct modulated laser, electro-absorption modulator, or any other suitable component to modulate the laser light thereby forming the probe beam that is split into object and reference beams.

By switching the right-most beam splitter 118 in FIG. 1A to direct the incoming light towards left instead of right, the bulk interferometer 104 becomes a Sagnac interferometer. The Sagnac interferometer is very stable because both reference and object beams are counter propagating, both hitting the sample, and travel through the same light path. Accordingly, Sagnac interferometer is not as sensitive to changes that occur in the object as a Mach-Zehnder or a Michelson interferometer.

Figure 2A:
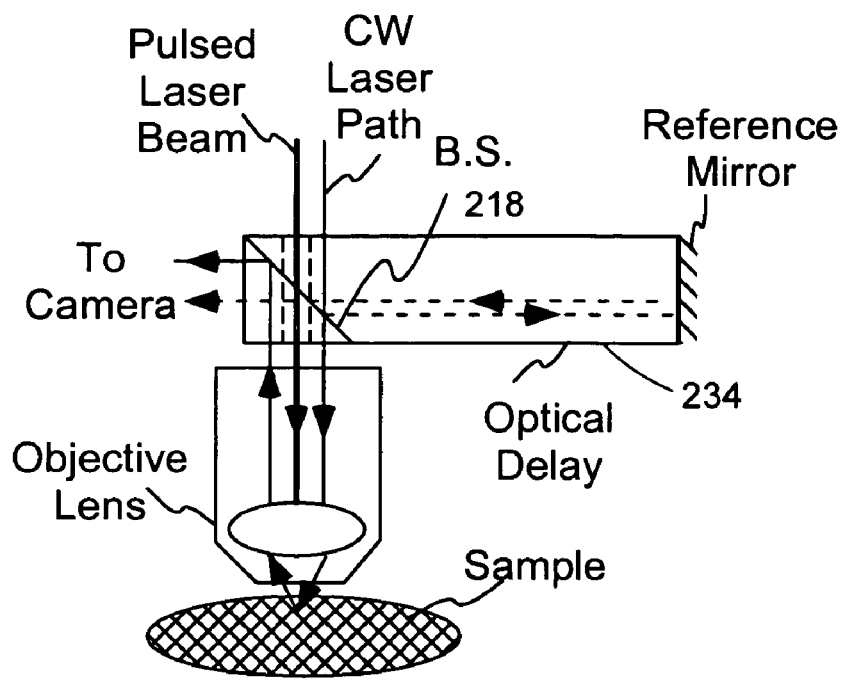
FIGS. 2A and 2B are schematic pictorial diagrams showing respective side and detail perspective views of a combined beam splitter/reflector that can optionally be used in the interferometer shown in FIG. 1A.
Figure 2B:
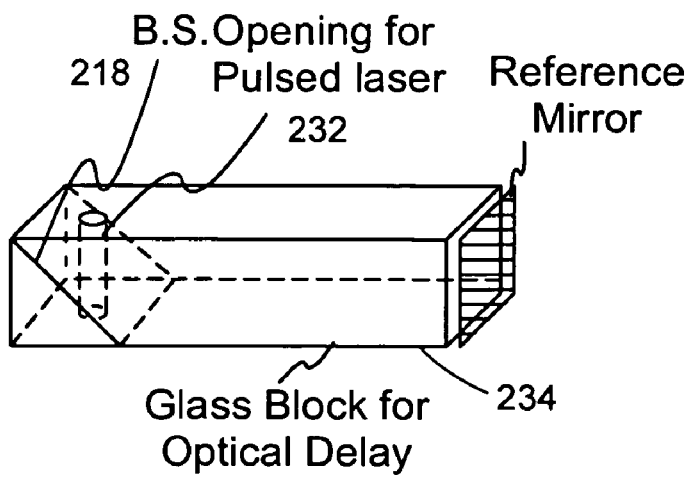

Referring to FIGS. 2A and 2B, schematic pictorial diagrams show respective side and detail perspective views of a combined beam splitter/reflector 218 that can optionally be used in the interferometer 104A shown in FIG. 1A. The illustrative glass block/beam splitter 218 supplies reflection, optical delay, and a clear pathway to the pulsed laser through an opening 232 in the glass. For added stability and compactness a reference arm 234 can be glass instead of a free space. Glass refractive index is approximately 1.5 compared to vacuum refractive index of 1. Therefore, the reference arm length can be much shorter in glass than in free space. In addition, using glass forms a mechanically more stable architecture. Both the Michelson 104B and Mach-Zehnder 104A interferometers can be implemented in glass. The Mach-Zehnder architecture is shown in FIGS. 2A and 2B with an opening 232 that can be used to pass the pulsed laser beam. The Michelson interferometer 104B can be implemented similarly without shifting the probe beam from the center of the optic axis. In this case, an opening in the middle of the beam splitter 218 is not necessary.

Figure 3A:
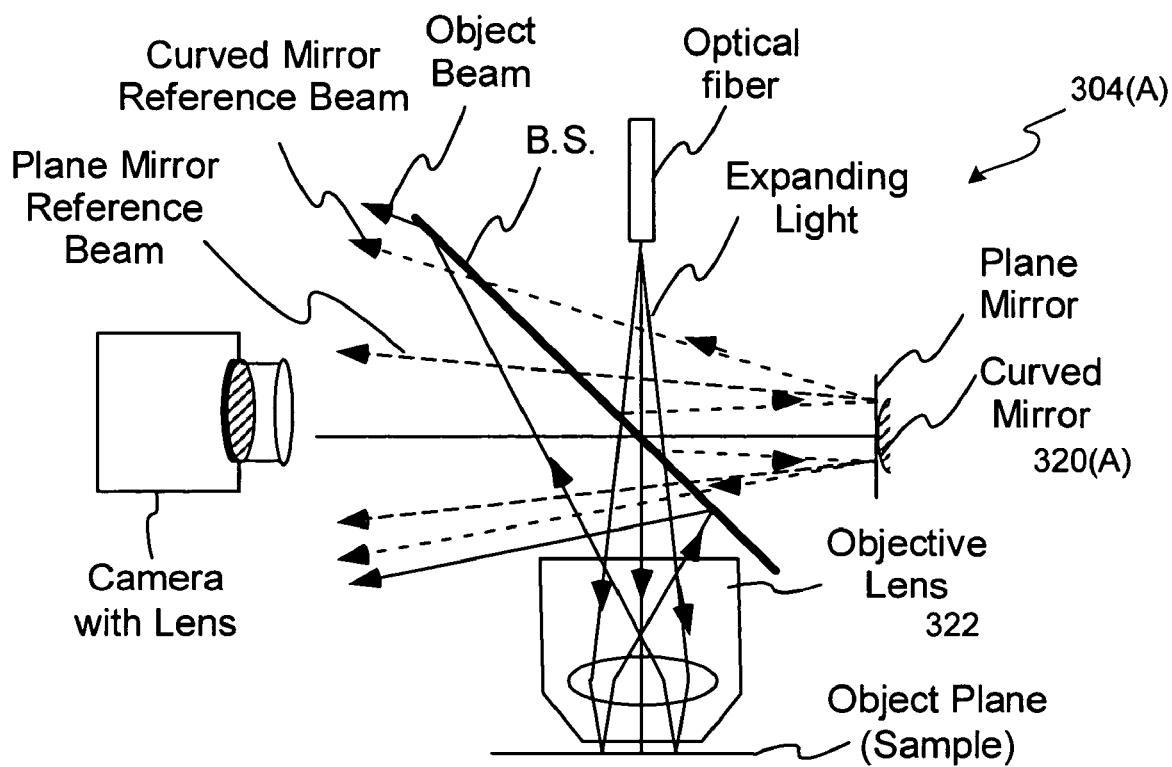
FIGS. 3A, 3B, and 3C are schematic mixed pictorial and block diagrams showing different configurations of an interferometer including details of system imaging capability.
Figure 3B:
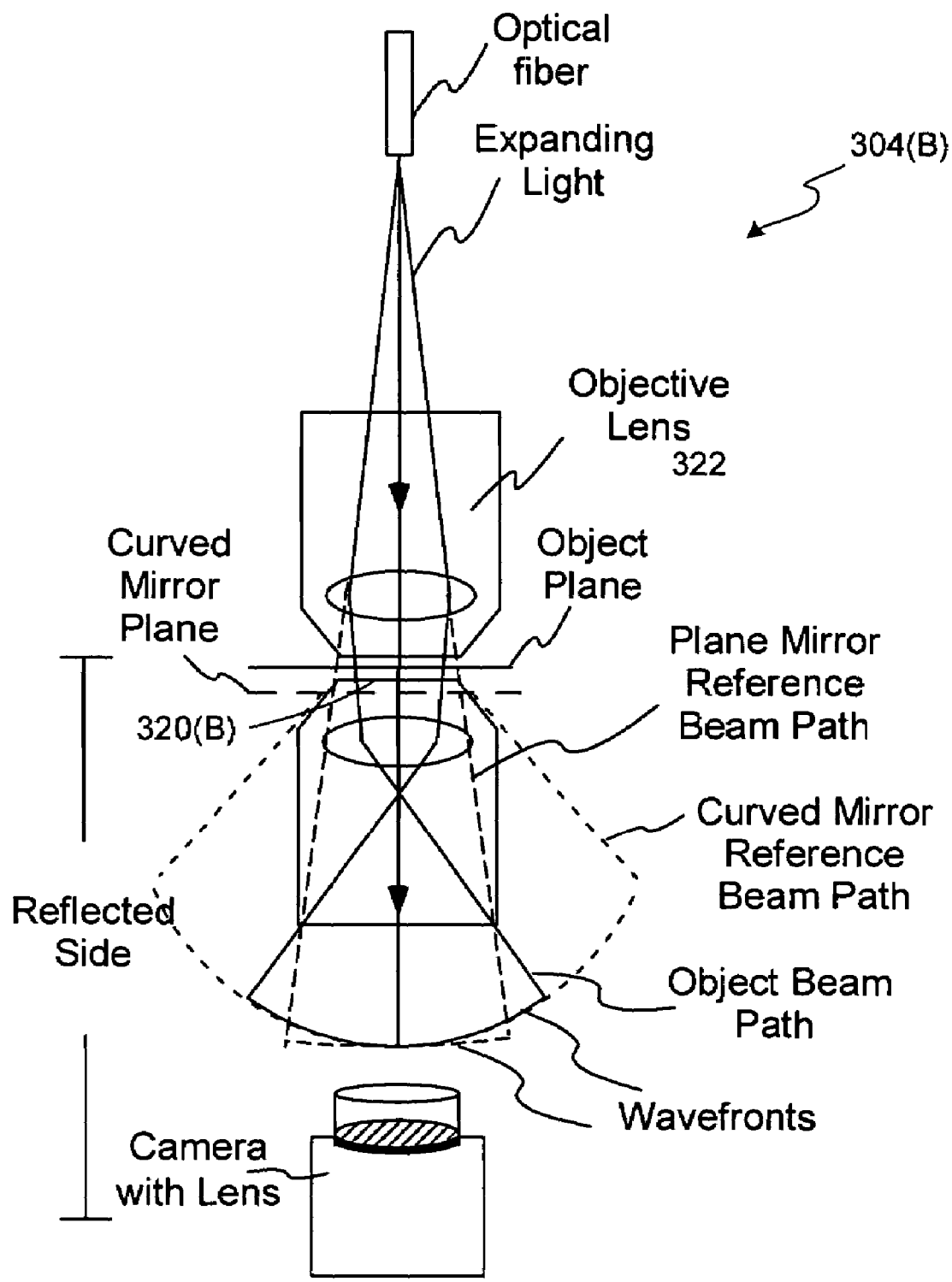
Figure 3C:
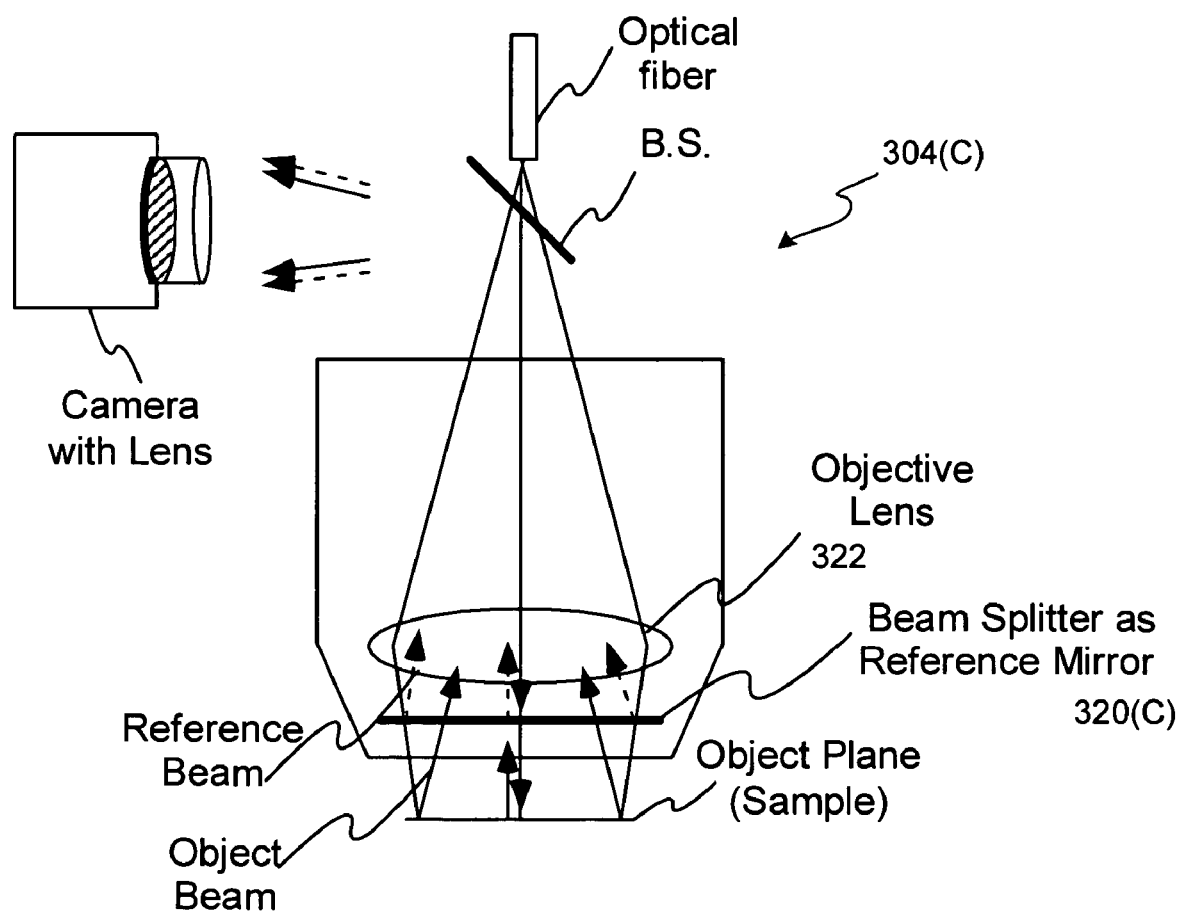

Referring to FIGS. 3A, 3B, and 3C, schematic mixed pictorial and block diagrams show different configurations of an interferometer 304 including details of system imaging capability. FIG. 3A depicts a configuration 304A using either plane or curved reference mirrors 320A. FIG. 3B shows a simplified illustration of an interferometer 304B with optical beam paths formed by unfolding the optical axis. When a curved mirror is used, the object and reference beam wavefronts are better matched in comparison with use of a plane reference mirror. FIG. 3C illustrates an interferometer 304C with a reference mirror 320C placed between the objective lens 322 and the object plane.

The details of imaging optical rays are shown in FIG. 3A. Two cases are illustrated, one using a plane mirror, and another using a curved mirror. The curved mirror enables better wavefront matching, thus producing linear rather than circular fringes at the camera. Another method to obtain linear fringes is to introduce an identical objective lens 322 in the reference arm and use a plane mirror, typically a more costly option. The details of the optical ray paths and the wavefront matching are shown in FIG. 3B, using an unfolding optical patch for added clarity. Another architecture 304C utilizes a reference mirror 320C between the objective lens 322 and the sample as shown in FIG. 3C, although contrast of the fringes may be reduced. If so, the pulsed laser can to be filtered in a manner similar to that shown in FIG. 1B to avoid saturating the camera.

In the configurations shown in FIGS. 1A and 1B, the pulsed laser beam is focused at the center of the sample 106. Although surface waves propagate outward across the sample, the bulk waves do not travel far. Therefore, multiple pulsed laser spots can be generated for a more complete analysis. The multiple pulse laser spots can be formed by placing a diffractive or holographic optical element (DOE or HOE) 436 in the path of the pulsed laser beam as shown in FIG. 4A.

Figure 4A:
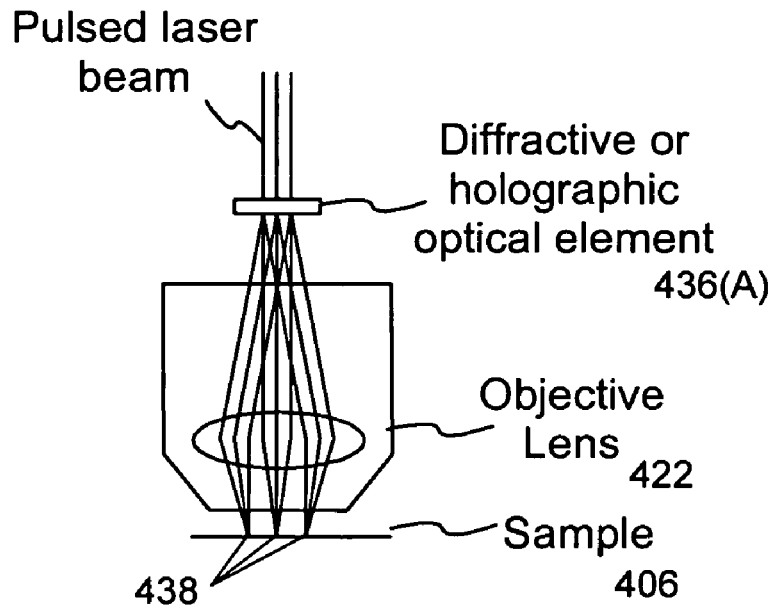
FIGS. 4A and 4B are pictorial diagrams illustrating two example embodiments of interferometer structures that can be used to control the shape, size, and form of sample illumination.
Figure 4B:
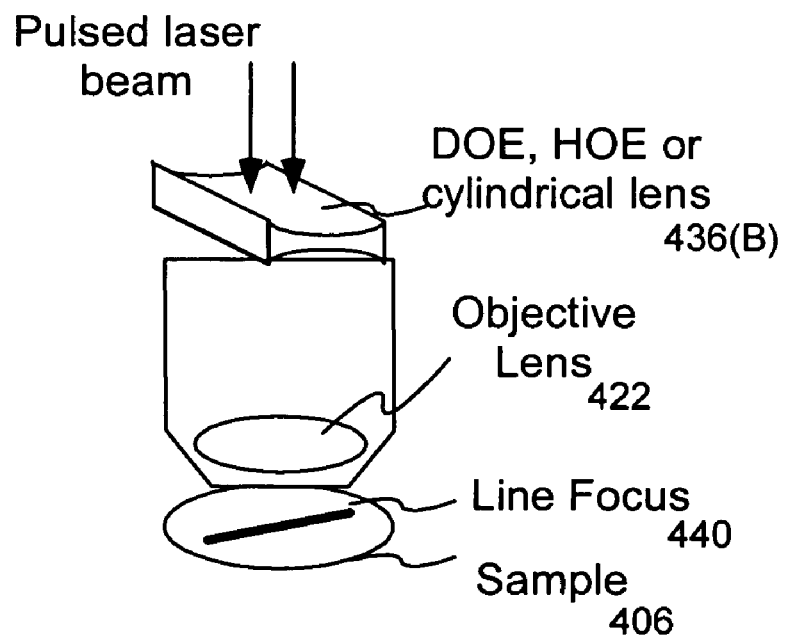

Referring to FIGS. 4A and 4B, pictorial diagrams show two examples of interferometer structures that can be used to control the shape, size, and form of sample illumination. FIG. 4A illustrates a structure and technique for generating multiple pulsed laser spots 438 using a diffractive or holographic optical element 436A. FIG. 4B illustrates a structure including a DOE, HOE, or cylindrical lens 436B for generating a line focus 440. The element 436 can be placed in the interferometer configuration in the pulsed laser beam path.

In some configurations, a sensing scheme that produces directional sensitivity may be useful. For example, one application is measurement of anisotropic variations in the sample 406, such as variations of the grain direction in the surface or subsurface, or for measurement of strain in the material. Accordingly, instead of using a DOE or HOE that generates multiple focus spots, an optical element can generate a line focus 440 as depicted in FIG. 4B. The line focus 440 can be formed using a positive or a negative cylindrical lens, an HOE or DOE 436B. Elastic waves such as surface acoustic waves propagate predominantly in the direction normal to the line focus 440. If the sample has anisotropy, the spatial acoustic signal varies as a function of angle. For example, if the sample is rotated, the acoustic signature varies and the information reveals the presence of anisotropy which can be further characterized.

The interferometric detection sensors 100 shown in FIGS. 1A and 1B have a resolution limited by the light diffraction. For example, the microscopic resolution, for example using an objective lens, is given by formula (1) as follows:

$$x_{min} = 0.61 \lambda / n \cdot \sin(\theta) \tag{1}$$

where $x_{min}$ is the optical resolution, $\lambda$ is the optical wavelength, n is the refractive index of the medium, and $\theta$ is angle of the optical rays. The medium is typically air. If an oil immersion system is used, the refractive index is the index of the oil. The denominator of equation (1) is the numerical aperture (NA) of the lens. For example, a 60× objective lens with NA of 0.85 at $\lambda$=633 nm has a resolution limit of 454 nm.

Figures 5A, 5B:
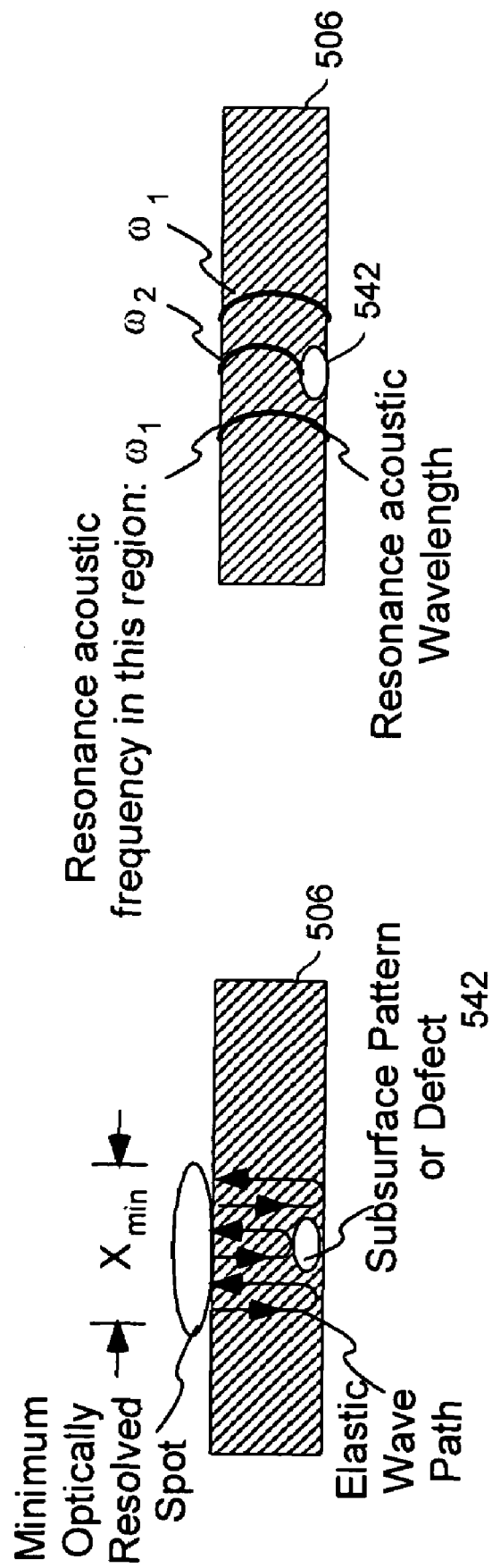
FIGS. 5A and 5B are cross-sectional pictorial views illustrating embodiments of techniques for resolution enhancement.
Figure 6A:
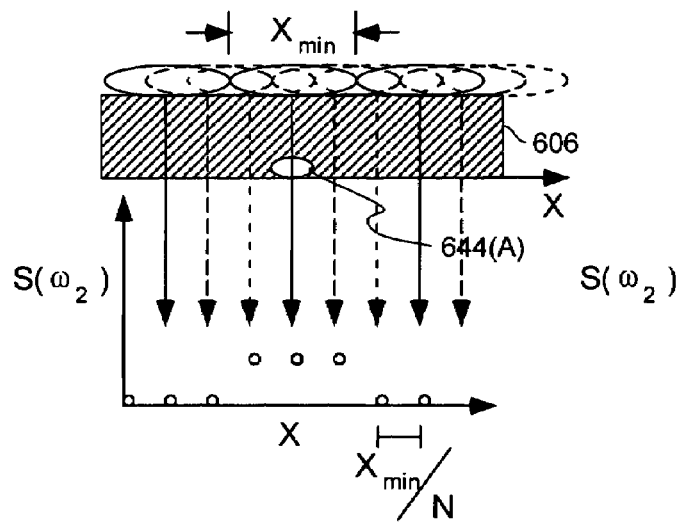
FIGS. 6A through 6D are cross-sectional pictorial views illustrating high-resolution detection of objects in a sample of different sizes.
Figure 6B:
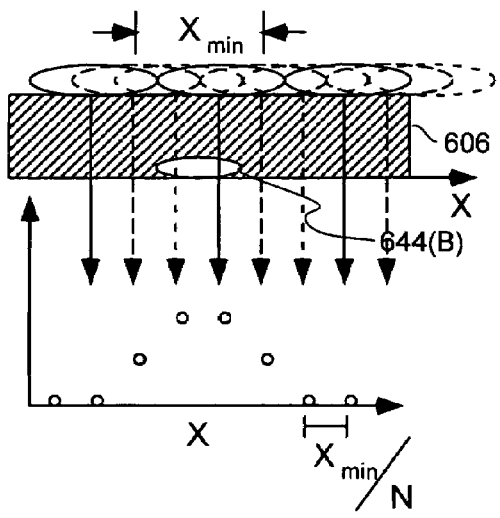
Figure 6C:
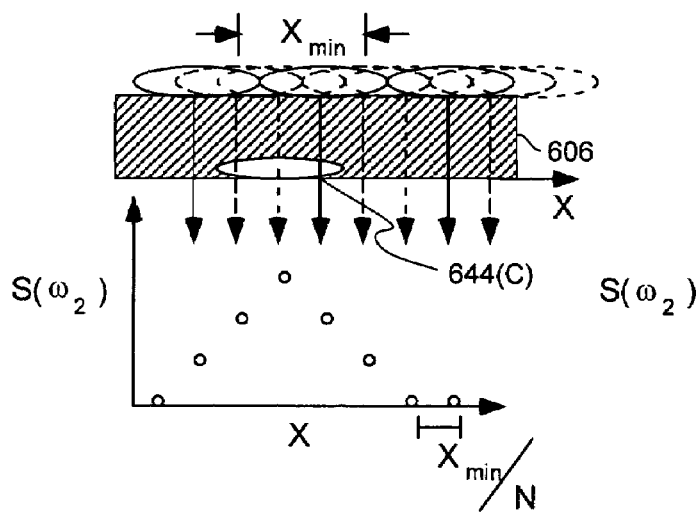
Figure 6D:
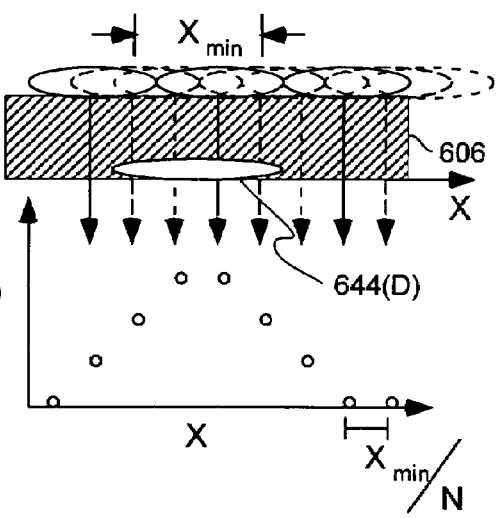

Referring to FIGS. 5A and 5B, cross-sectional pictorial views illustrate embodiments of techniques for resolution enhancement. FIG. 5A shows a geometry where the optically resolved spot $x_{min}$ is larger than the subsurface structure. FIG. 5B shows an example in which acoustic resonance varies in the vicinity of the subsurface feature. Thick lines indicate the fundamental acoustic resonance, the half-acoustic wavelength.

The optical resolution for the sensors 100 shown in FIGS. 1A and 1B is approximately 500 nm, but can be increased to obtain higher resolution by various techniques. One technique illustrated in FIGS. 5A and 5B and FIGS. 6A through 6D increases resolution by moving a sample at finer resolution steps than the optical resolution, and taking multiple measurements.

FIG. 5A shows a typical scenario, where the subsurface pattern, for example a void, is smaller than the optically resolved spot, $x_{min}$. Elastic waves are reflected at various interfaces.

The acoustic resonances vary spatially depending on the location of the void 542, as depicted in FIG. 5B, a characteristic that can be exploited by moving the sample 506 or the entire optical system at finer steps than the optically resolved spot. The signal at a given resonance frequency, for example at $\omega_2$, varies depending on the location where the pixel is centered, as depicted in FIGS. 6A through 6D.

Referring to FIGS. 6A through 6D, cross-sectional pictorial views illustrate high-resolution detection of objects 644A-644D in a sample 606 of different sizes. High-resolution detection is performed by moving the sample 606 or the optical system at finer steps than the optical resolution limit. Moving the sample 606 or the optical system at much finer steps than $x_{min}$ produces a signature that varies in shape and amplitude depending on the size of the object 644A-644D. Observing the signature variation reveals the size and exact location of the object 644A-644D at higher than optical resolution.

Figure 7A:
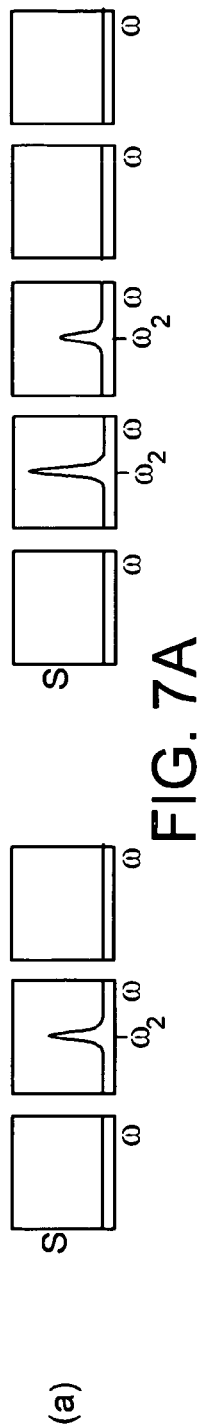
FIGS. 7A through 7D are spectral and pictorial diagrams showing sub-surface feature or defect detection at higher than optical resolution by comparing of the spectra in each pixel and neighboring pixels.
Figure 7B:
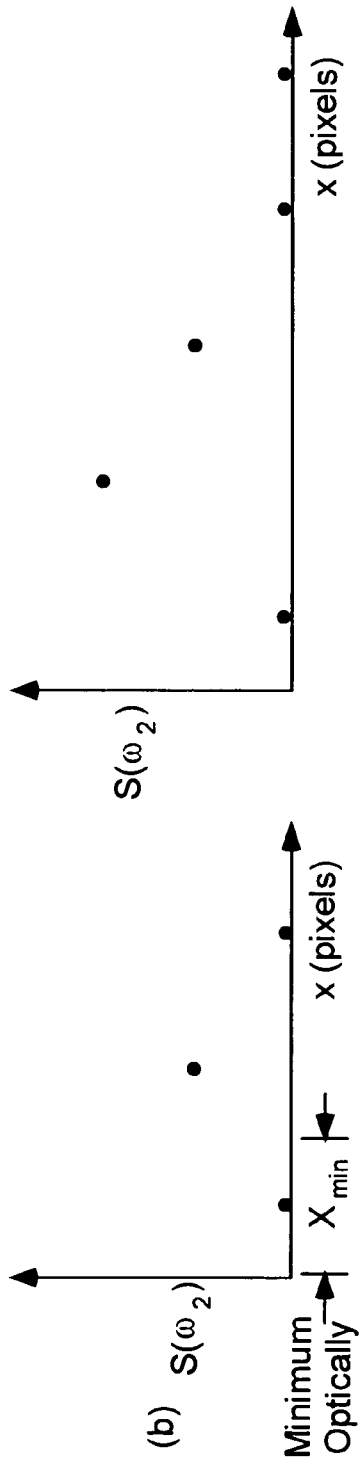

Referring to FIGS. 7A through 7D, spectral and pictorial diagrams illustrate sub-surface feature or defect detection at higher than optical resolution by comparing of the spectra in each pixel and neighboring pixels. FIG. 7A shows acoustic spectra at each pixel of samples shown in FIGS. 7C and 7D. Amplitude at the resonance frequency is shown in FIG. 7B. Samples shown in FIGS. 7C and 7D contain different size voids 746C and 746D.

Figure 7D:
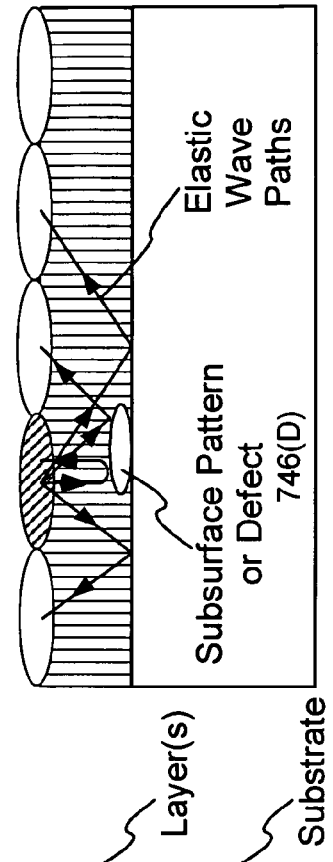
Figure 7C:
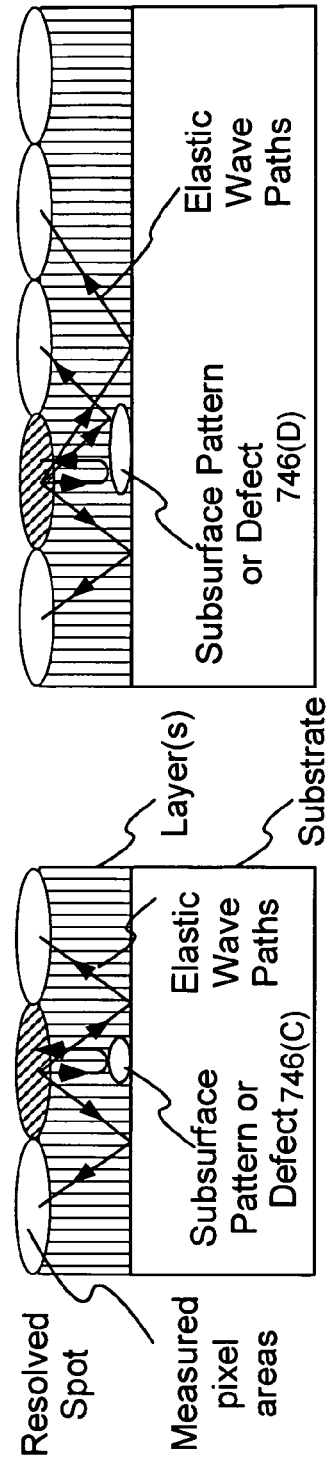

A second approach to achieve higher resolution than $x_{min}$ is involves observation of the signal at nearest neighbor pixels. In certain geometries, elastic waves generated at one pixel reach the nearest neighbor pixels, enabling detection of higher resolution information than the optical limit as depicted in FIGS. 7A through 7D. The elastic wave can be generated at the hatched area by the focused pulsed laser beam. The elastic wave travels into the medium, reflects at the interface of the embedded patter such as a void 746, and reflects back to the surface detected by the interferometric system. A portion of the elastic wave also travels at an angle and is reflected to adjacent pixels. Observing the variation of the spectrum or the amplitude of the detected signal at a specific frequency $\omega_2$ from neighboring pixels reveals the size of the subsurface pattern, along with shape, type, and other physical parameters. The nearest neighbor measurement method is depicted in FIGS. 7A through 7D. As shown in FIGS. 7C and 7D, the detected signal amplitude and shape is clearly different between voids of different sizes, even if the void is smaller than $x_{min}$.

Figure 8:
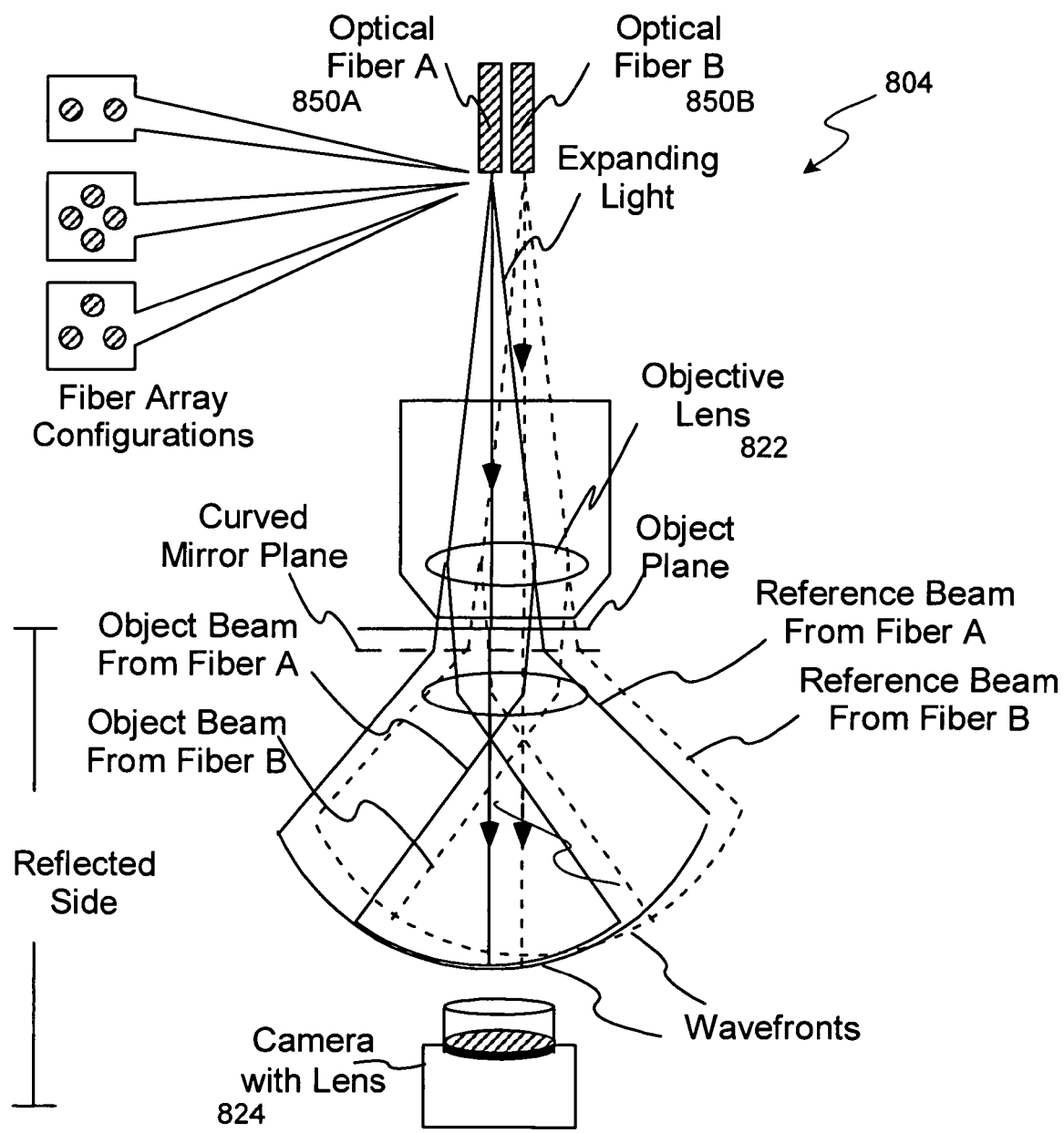
FIG. 8 is a schematic pictorial and block diagram illustrating an embodiment of an interferometer that obtains higher resolution than $x_{min}$ by using multiple input fibers.

Referring to FIG. 8, a schematic pictorial and block diagram shows an embodiment of an interferometer 804 that obtains higher resolution than $x_{min}$ by using multiple input fibers 850A and 850B. For clarity, FIG. 8 shows an unfolded optical path. In an illustrative implementation, a beam splitter can be used in the optical path as described in with reference to FIG. 1B which directs the reflected light from the sample to the camera 824. Multi-fiber array illumination enables high-resolution measurements. The interferometer 804 has an unfolded optical path that is similar to that shown in FIG. 3B. A modulator positioned in the optical path prior to the fibers 850A and 850B is omitted to promote clarity. A fiber array configurations inset shows cross-sectional views of various types of fiber arrays, for example two, three, and four fiber arrangements. Adjacent fibers produce multiple fringe sets which can be used to further enhance the detection resolution.

Figure 9A:
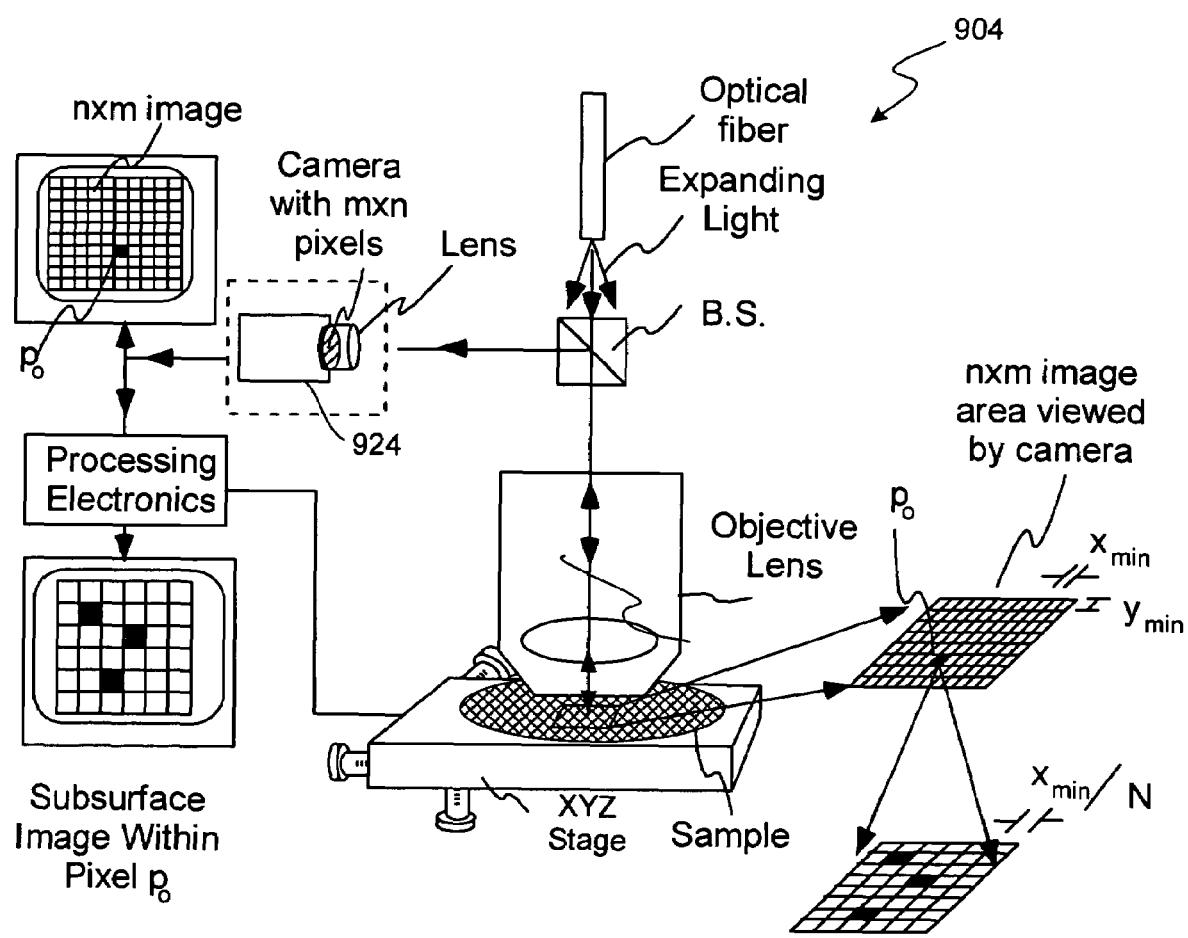

Referring to FIG. 9A, a schematic pictorial and block diagram shows an embodiment of an interferometer 904 that enables analysis and enhancement of scan speed. The diagram illustrates a structure for determining measurement speed, while omitting the reference mirror and reference beam path to promote clarity. The system 904 measures m×n spots which are limited by the optical resolution $x_{min}$ and the camera detector pixel dimensions. For higher resolution measurements using the scheme described in FIGS. 6A-6D, the stage or the entire optical system move at finer resolution steps $x_{min}/N$.

In one example configuration, if the optical resolution $x_{min}$ is 500 nm and the desired measurement resolution is 50 nm, then each pixel is subdivided to 10 divisions, specifically 10×10 movements in x and y directions. Assume the camera 924 operates at a maximum speed of 5 MHz (0.1 microsecond) and has 1000×1000 pixels. Two example cases are considered, first the time duration for scanning a 1 cm² area, and second the time duration for scanning a 300 mm diameter wafer. Both lower and upper limits can be calculated. The fastest time is attained when no other bottlenecks occur and each 1000×1000 image takes 0.1 microsecond to capture and process. The slowest time occurs if each 1000×1000 image takes 1 millisecond to obtain and the system is limited primarily by the mechanical stage movement time. Results of the calculations are shown in Table I depicted in FIG. 9B.

As shown in Table I, a 1 cm² spot can be measured in 0.4 seconds even at a measurement speed is 1 ms. Similarly, an entire 300 mm waver can be scanned in 4.71 minutes even for a scan time of 1 ms. At 0.1 microsecond detection speed, the scan time is much faster (0.09 min) as shown in Table I.

Referring to FIGS. 10A, 10B, and 10C, schematic pictorial diagrams illustrate embodiments of interferometer structures that can be used to interrogate a large area at a very rapid rate via methods of integration for massively parallel detection. A multi-element measurement can be achieved using array approaches shown in FIGS. 10A, 10B, and 10C. Three cases are shown. The structure shown in FIG. 10A has a fiber array including a 1×N fiber multiplexer 1052A. The structure of FIG. 10B has a modulator array 1052B for example integrated waveguide modulators. The structure shown in FIG. 10C includes refractive, diffractive (DOE) and holographic (HOE) optical elements 1052C to create multiple beams. Each example embodiment includes multiplexed objective lenses 1022, along with multiple beam splitters 1018, and compact cameras 1024, enabling a large area to be measured simultaneously, thus substantially reducing the measurement time.

Figure 11B:
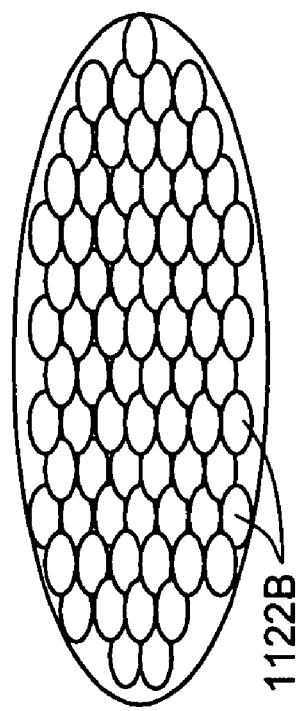
FIGS. 11A and 11B are pictorial diagrams illustrating embodiment configurations for multiplexing objective lenses in interferometer structures.
Figure 11A:
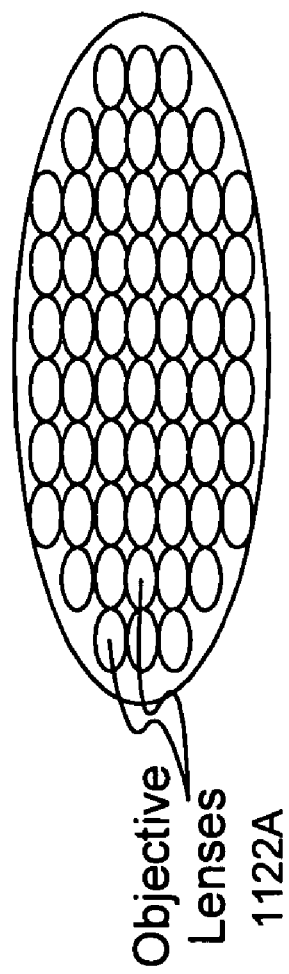

The objective array, as well as the fiber or waveguide array, can be constructed using various geometries. Referring to FIGS. 11A and 11B, pictorial diagrams illustrate embodiment configurations for multiplexing objective lenses 1122 in interferometer structures. FIG. 11A depicts objective lenses 1122A in a square grid. FIG. 11B shows objective lenses 1122B in offset grid patterns.

Figure 12:
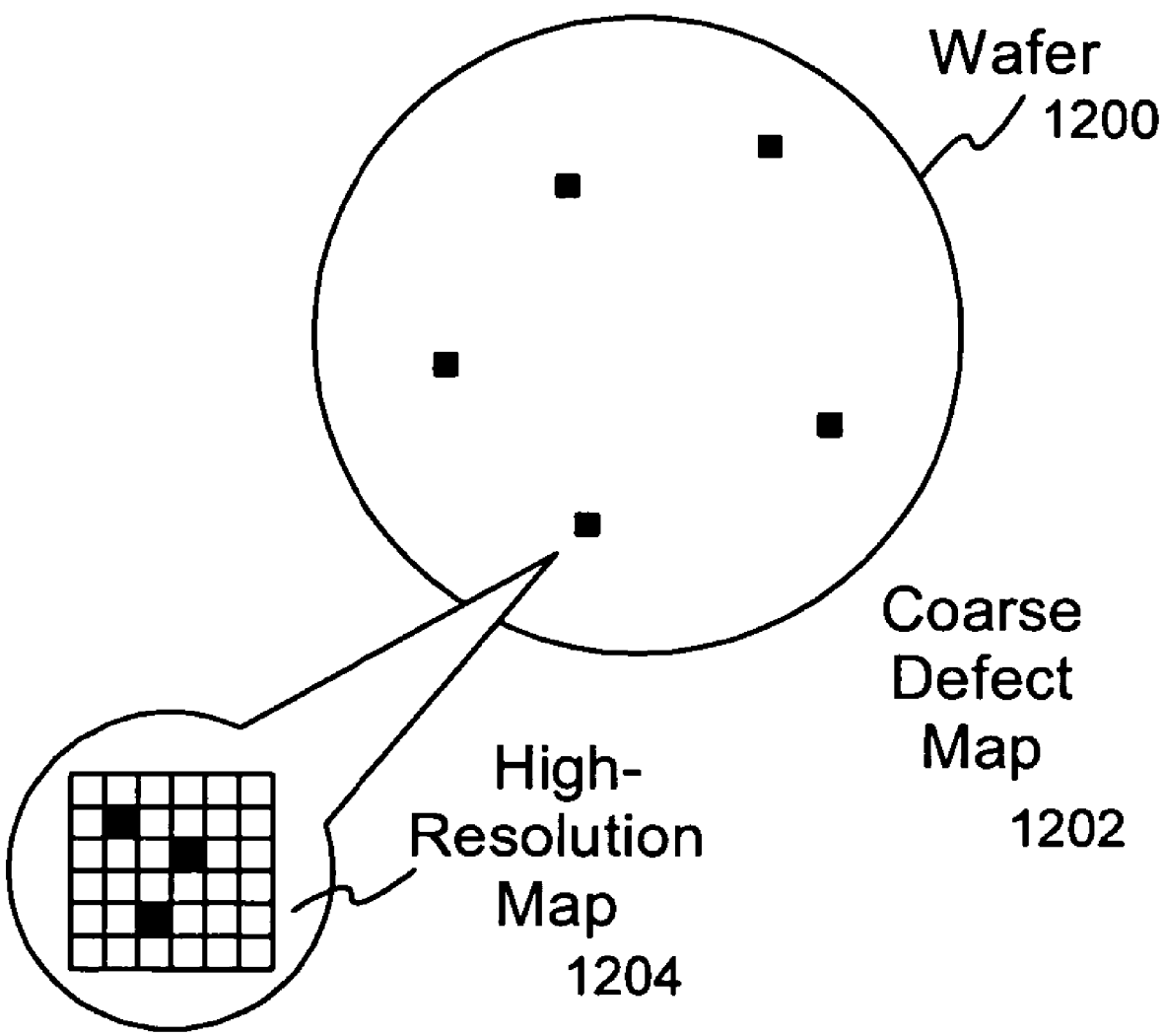
FIG. 12 is a schematic pictorial diagram that shows an example embodiment of a technique for determining defect location on a wafer with coarse resolution and high-resolution scans.

Referring to FIG. 12, a schematic pictorial diagram illustrates an example embodiment of a technique for determining defect location on a wafer 1200 with coarse resolution and high-resolution scans. The technique reduces measurement time by performing the measurements in two stages. First a coarse measurement is taken to produce a coarse defect or wafer map 1202 and, if one or more defects are observed in the wafer map 1202 then fine measurement is taken only where defects are present to produce a high-resolution map 1204.

Referring to FIGS. 13A, 13B, 14A, 14B, 15A, 15B, 16A, 16B, 17A, and 17B include cross-sectional pictorial views that illustrate examples of metrology applications that can be performed using the acoustic spectrum analysis sensors 100A and 100B depicted in FIGS. 1A and 1B.

The sensors 100A, 100B can be used to acquire subsurface structural information by illuminating a sample under test with a pulsed laser signal that propagates a shock wave through the sample, and then by measuring a surface vibration signature of a micro or nano structure of the sample induced by the pulsed laser signal. In another example, the sensors 100A, 100B can acquire subsurface structural information by illuminating a multiple-layer sample under test with a pulsed laser signal that excites elastic waves propagating normal to a sample surface, reflecting from multiple-layer surfaces back to the surface. Changes in refractive index near a surface of the sample under test induced by the pulsed laser signal can then be measured.

Figure 13B:
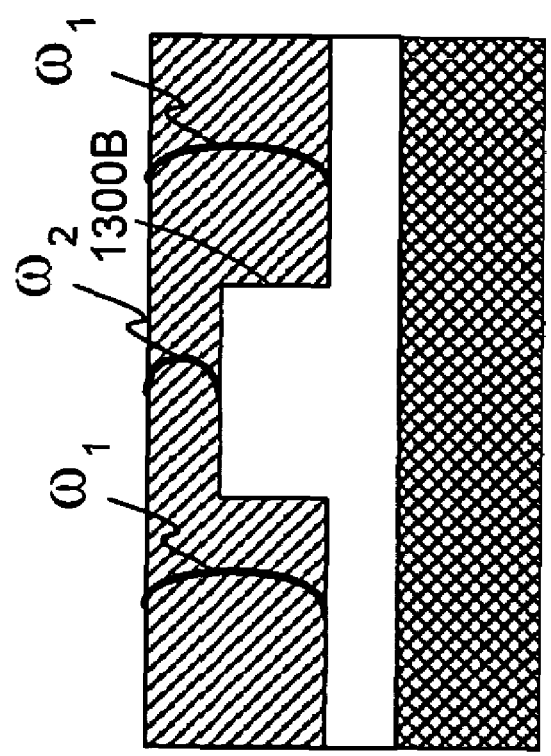
FIGS. 13A and 13B are cross-sectional pictorial views that illustrate a metrology technique using acoustic resonances to detect surface and sub-surface patterns, respectively.
Figure 13A:
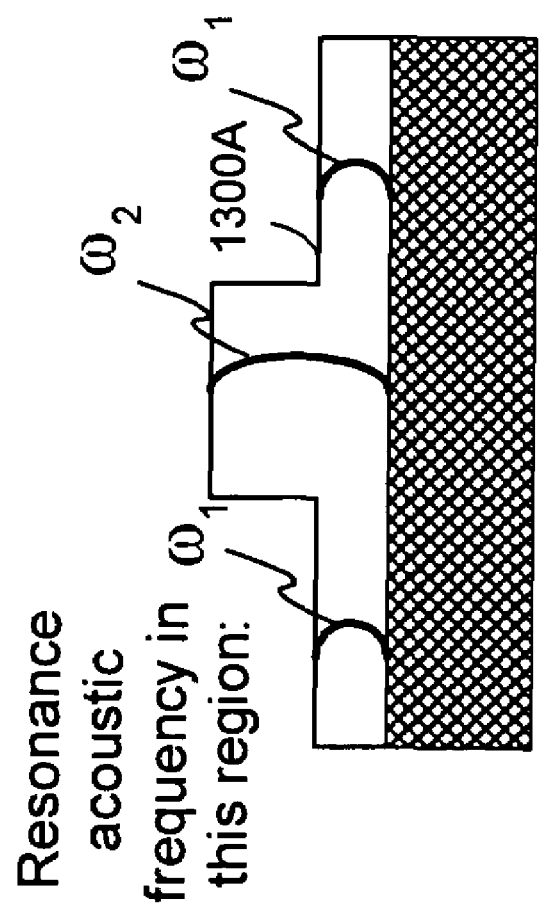

Referring to FIGS. 13A and 13B, acoustic resonances can be used to detect surface and sub-surface patterns, respectively. The sensors 100A, 100B can be used to detect lines and features in the surface and subsurface of a wafer, as well as the line shape, slope, line-edge roughness and other parameters. Cross-sectional views show surface lines 1300A in FIG. 13A and subsurface lines 1300B in FIG. 13B with corresponding acoustic resonances of $\omega_1$ and $\omega_2$. Resonances are result of acoustic discontinuity between the top layer and air, and the discontinuity between the top layer and the substrate, or the layer directly below the top layer. In FIG. 13A, the top layer is shown as the patterned layer. In FIG. 13B, the patterned layer is buried under the top layer. In general, additional resonances can result from other interfaces, but the resonances can be distinguished by the signal strength and/or frequency content. Post detection signal processing enables filtering to remove the unwanted data.

Figures 14A, 14B:
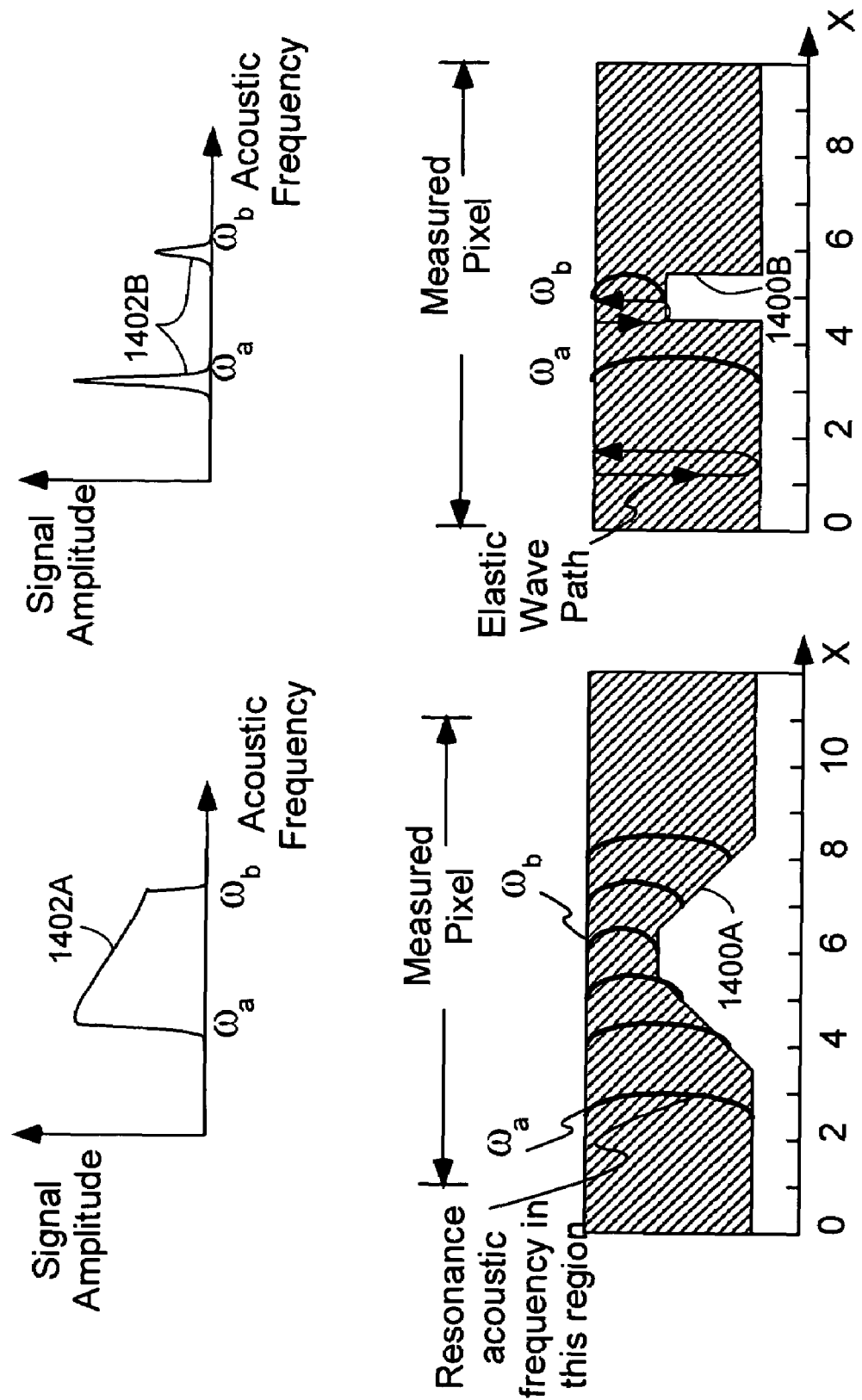
FIGS. 14A and 14B are cross-sectional pictorial views and corresponding spectral graphs illustrating a metrology method for usage in coarse resolution detection whereby the pixel or optically resolved spot is larger than the feature.

Referring to FIGS. 14A and 14B, cross-sectional pictorial views and corresponding spectral graphs illustrating a metrology method for usage in coarse resolution detection whereby the pixel or optically resolved spot is larger than the feature. A line with slope 1400A is shown in FIG. 14A and a line that approximates a step function 1400B is shown in FIG. 14B, along with corresponding spectra 1402A and 1402B, respectively, obtained from the measurement of the pixel. Acoustic resonances $\omega_a$ and $\omega_b$ correspond to the acoustic resonance in the thick and thin sections of the upper layer, respectively.

For coarse resolution detection, for example if the feature is narrower than the optical resolved spot or the detection pixel, then an average response will be obtained as depicted in for lines thinner than the pixel, for example the sloped line 1400A in FIG. 14A, and the a step or straight edged function 1400B in FIG. 14B. The frequency response is substantially different for a line with straight edge 1402B versus a line with a slope 1402A. The sloped line 1400A has a broad spectral response 1402A because the resonance frequency in the slope region varies between $\omega_a$ and $\omega_b$. The acoustic frequency response is shown for a buried layer. Similarly, if the layer containing the line feature is an upper-most layer, the frequency response will also be different using the upper layer detection scheme depicted in FIG. 13A.

Figure 15B:
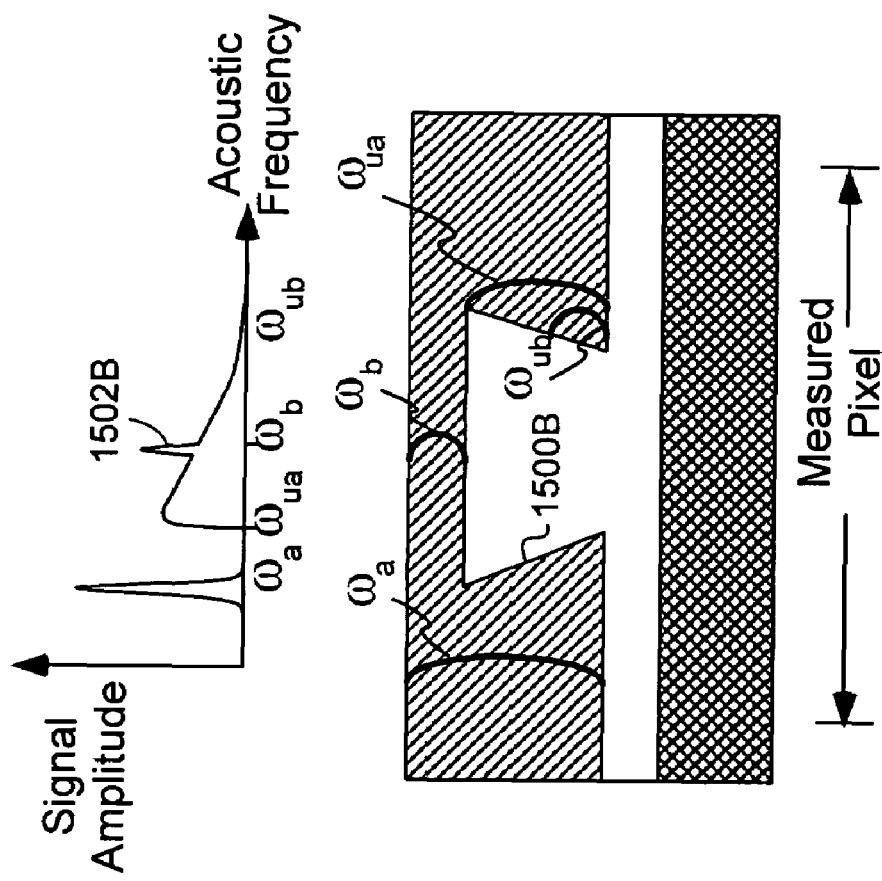
FIGS. 15A and 15B are cross-sectional pictorial views and corresponding spectral graphs depicting undercut lines and corresponding acoustic spectra.
Figure 15A:
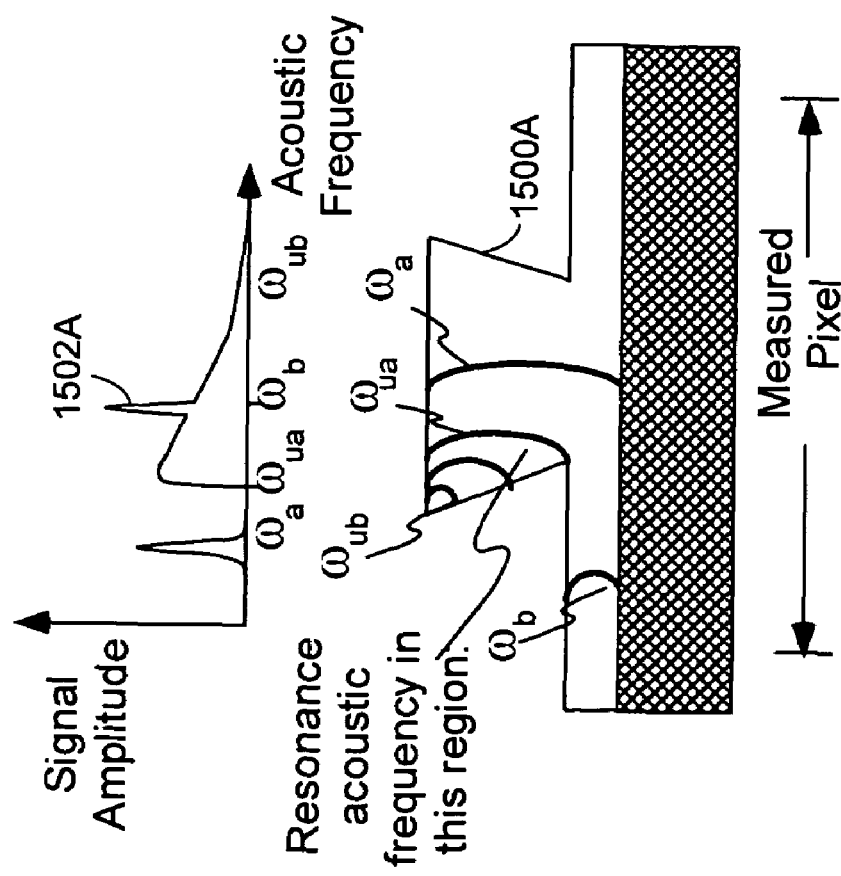

Referring to FIGS. 15A and 15B, cross-sectional pictorial views and corresponding spectral graphs depicting undercut lines and corresponding acoustic spectra. FIG. 15A shows an undercut line 1500A at the surface. FIG. 15B depicts a buried undercut line 1500B. Acoustic spectra $\omega_{ua}$, $\omega_{ub}$ illustrate a range of frequency components 1502A and 1502B, respectively, due to the undercut region. If the line has an undercut, the acoustic frequency response is different as compared to a positive slope. FIG. 15A shows an undercut line 1500A contained in an upper layer. FIG. 15B depicts a buried undercut line 1500B. The shape of the spectrum indicates the undercut angle.

Referring to FIGS. 16A and 16B, cross-sectional pictorial views and corresponding spectral graphs depicting line-edge roughness detection. FIG. 16A shows a rough-edged line 1600A. FIG. 16B illustrates a buried line 1600B that is rough-edged. Acoustic spectra $\omega_{ra}$, $\omega_{rb}$ illustrate a range of frequency components 1602A, 1602B produced by line edge roughness for surface and buried lines, respectively. In general, breadth of the spectral lines is indicative of line edge roughness.

Referring to FIGS. 17A and 17B, cross-sectional pictorial views and corresponding spectral graphs illustrate a technique for high-resolution detection by moving a sample or the optical system at step sizes finer than the optical resolution limit. FIG. 17A shows a sloped line and FIG. 17B illustrates straight edged line or step function type line. Spectra $S(\omega_i)$ correspond to the signal at frequency $\omega_i$.

FIGS. 14A, 14B, 15A, 15B, 16A, and 16B illustrate metrology with lines narrower than the detection or pixel resolution. Metrology can also be used for higher than optical resolution detection using the techniques described with respect to FIGS. 6A-6B, 7A-7B, and 8. Resolution higher than pixel resolution can be detected using the moving sample technique described with respect to FIGS. 6A-6B as depicted in FIGS. 17A and 17B which show two buried lines, one with a slope in FIG. 17A, and another without a slope in FIG. 17B. The sloped line produces multiple frequency components, while the non-sloped line produces only two frequency components, for example components $\omega_1$ and $\omega_4$. The fine movement data yields higher than optical resolution information, whereas the spectral data yields the line shape. Combination of the two sets of data yields higher than optical resolution shape and size information.

The signal obtained in FIGS. 17A, 17B is a correlation or convolution of the optical window or pixel and spectral response of the line feature. For example, in FIG. 17B signal $S(\omega_4)$ is a correlation or convolution of the optically resolved spot, for instance a pixel, and the rectangular function representing the line pattern. Therefore, to obtain the shape and size information from the observed spectra, the data can be fitted using a correlation or convolution operation. To increase the calculation speed, the correlation or de-correlation can be performed in the 1/x space using Fast Fourier Transforms (FFT). Correlation or convolution in x space corresponds to multiplication in 1/x space, and multiplication is a much faster operation than correlation.

The acoustic sensor can be configured to perform various acoustic excitation methods. FIGS. 1A and 1B show sensors with acoustic excitation supplied using a pulsed laser. The technique can use other acoustic excitation structures and methods. Acoustic excitation can also be supplied by other devices including a flash-lamp, an arc-lamp, a thermal source, and an acoustic source such as a piezo-electric element. Thermal excitation can be attained either using a thermal pulse, or by heating the sample to increase thermal noise which is then converted to resonant acoustic frequencies. Thermal noise is white noise with broad spectral response. Various devices and techniques for acoustic excitation include, for example, pulsed laser, flash-lamp, arc-lamp, thermal pulse heating of the sample, and thermal excitation using thermal pulse, to attain acoustic excitation through thermal agitation of electrons in the material. Acoustic excitation heats the sample to increase thermal noise which is then converted to acoustic resonance.

Various sensor embodiments can be implemented using polarization optics. The architectures described herein use standard beam splitters and non-polarizing optics. Other example sensor configurations can use polarization optical components for better light control. For example, polarization components can be used in the pump and probe beam paths to facilitate separation of the pump and probe beam. If the pump beam is polarized in the x-direction and the probe beam is polarized in the y-direction, a polarizer placed in front of the camera that only passes y-polarized light avoids leakage of the pump beam to the camera. Thus the signal-to-noise ratio is higher than without using polarization optics.

Use of polarization optics typically also results in improved anisotropic measurements, for example as described with respect to the discussion of FIGS. 4A and 4B. If surface acoustic waves are used for anisotropic measurements, the reflected probe beam amplitude will have some dependence on the light polarization components. In addition, use of polarization optics allows detection of elastic wave induced birefringence, yielding additional information aside from the acoustic spectra.

Various sensor embodiments and implementations can be configured to perform phase sensitive measurements. When elastic waves travel a particular distance, a time delay occurs between the arriving acoustic signal compared to the generation signal due to the time interval for the elastic wave to travel in the material at a particular path. Measuring the time delay can give additional information about the location of a particular surface or subsurface structure.

The illustrative detection method is a frequency domain measurement. However, time delay in temporal domain corresponds to phase delay in the frequency domain. Therefore, detection of phase delay can be converted into time delay information by Fourier analysis, a detection technique that yields both amplitude and phase of the acoustic resonances. Measuring both amplitude and phase yields more information than an amplitude measurement alone.

For example, a $\pi$ phase shift in the frequency domain corresponds to half acoustic wavelength ($\lambda_a$) shift of $n\lambda_a/2$, where n=1, 3, 5, thus indicating that the elastic waves traveled a multiples of $n\lambda_a/2$. In a particular example measurement, for a resonance generated from a surface or subsurface structure, such as a buried void, with a particular resonance frequency and the resonance has a phase delay of $n\lambda_a/2$, then the feature is located at a distance that causes the elastic wave to have a delay of $n\lambda_a/2$. If the material parameters such as elastic wave velocity are known, the object location can be determined.

Figure 18A:
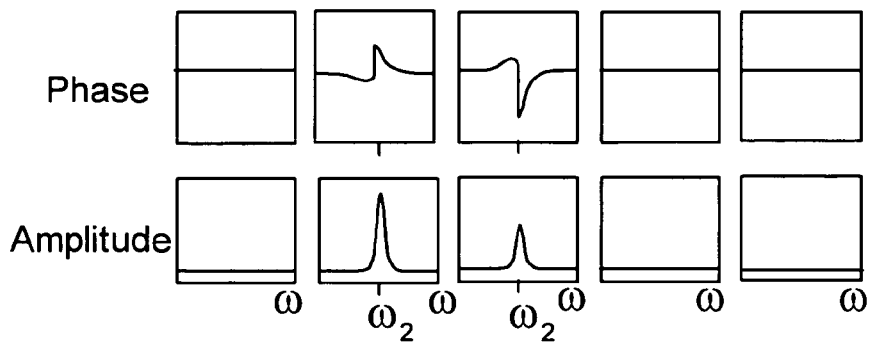
FIGS. 18A, 18B, and 18C, are a spectral graph, amplitude and phase plots, and a cross-sectional view of a sample respectively illustrating sub-surface feature or defect detection using phase and amplitude information from adjacent pixels at higher than optical resolution by comparing spectra in each pixel and neighboring pixels.
Figure 18B:
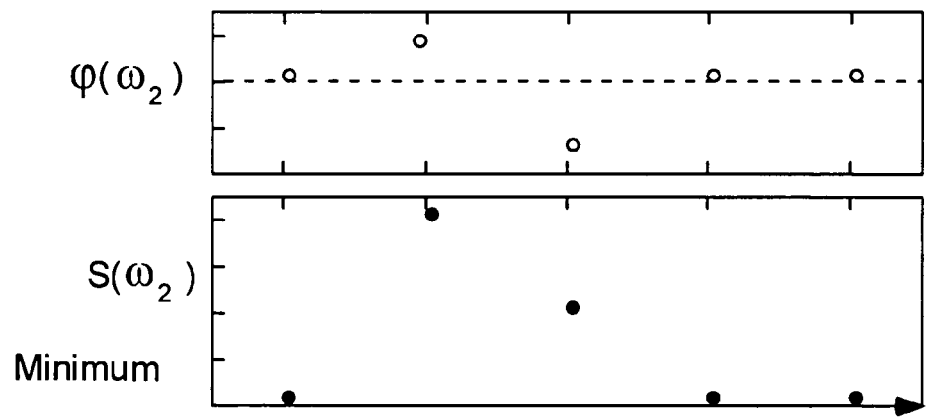
Figure 18C:
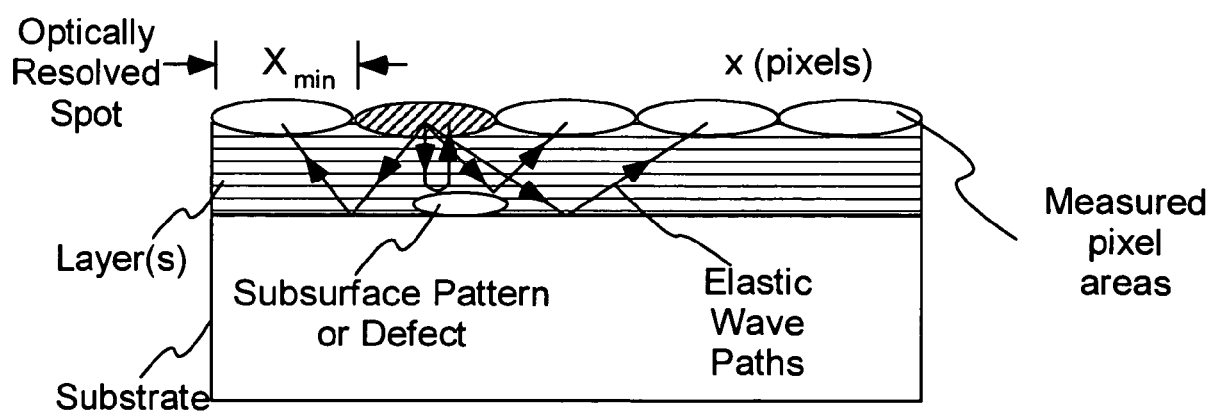

Phase measurements yield information about the location and depth of the subsurface structure. Referring to FIGS. 18A, 18B, and 18C, a spectral graph, amplitude and phase plots, and a cross-sectional view of a sample respectively illustrate sub-surface feature or defect detection using phase and amplitude information from adjacent pixels at higher than optical resolution by comparing spectra in each pixel and neighboring pixels. FIG. 18A shows acoustic spectra at each pixel of the sample shown in FIG. 18C. FIG. 18B illustrates amplitude S and phase φ at the resonance frequency. FIG. 18C is a cross-sectional view of a sample illustrating a measurement schematic.

By comparing phase and amplitude information of a pixel with its neighboring pixels, higher-than-optical resolution is achieved. FIGS. 18A-18C depict an example of a phase detection scheme that compares phase delay of nearest neighboring pixels. Another architecture that measures phase delay and compares the phase delay to delay of nearest neighbor pixels can use multiple Michelson-based sensors in parallel. A third architecture that can achieve phase sensitive measurement is shown in FIG. 19.

Figure 19:
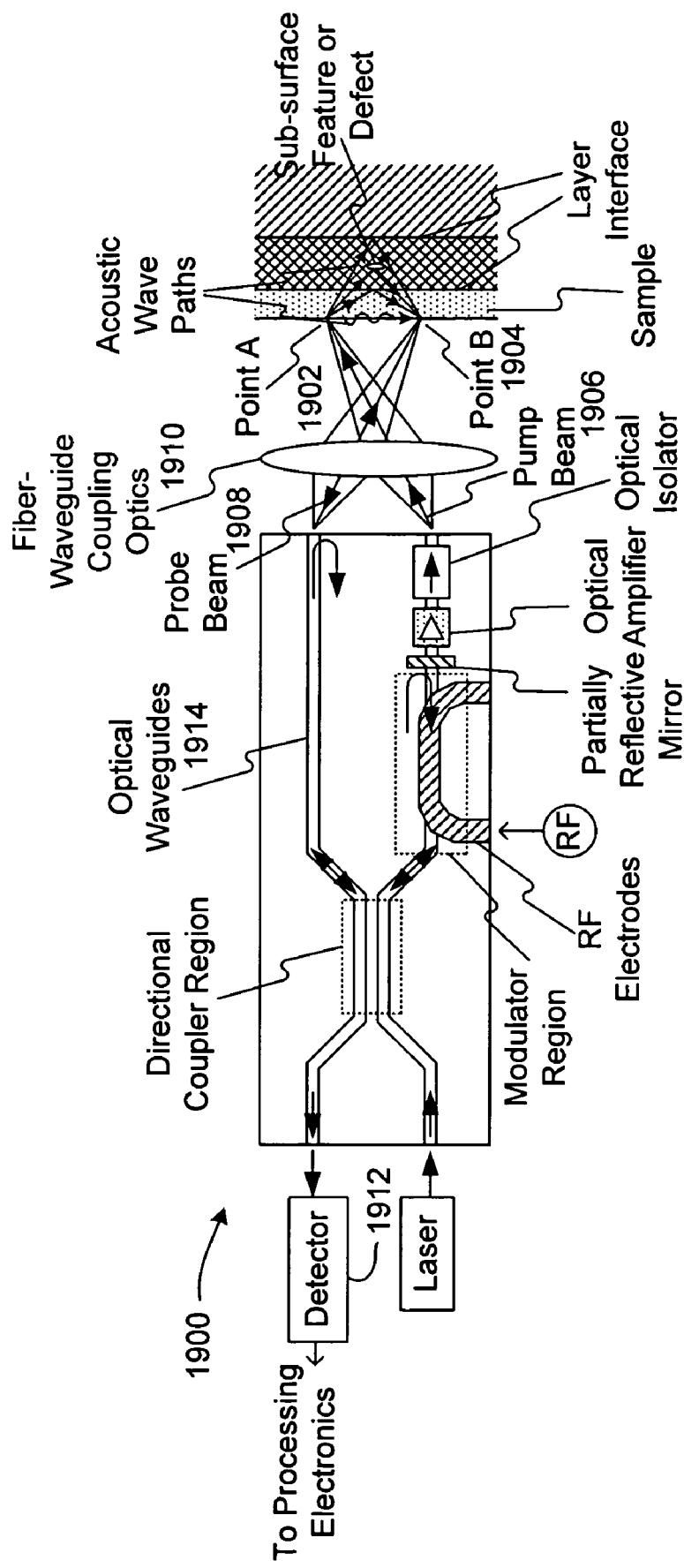
FIG. 19 is a schematic cross-sectional pictorial view that shows an example of architecture of a sensor that can be used for phase sensitive measurement.

Referring to FIG. 19, a schematic cross-sectional pictorial view shows an example of architecture of a sensor 1900 that can be used for phase sensitive measurement. The illustrative sensor 1900 has a Michelson interferometer architecture, an approach that is applicable for detection using any acoustic excitation scheme. Specifically, excitation can be supplied by an external laser pulse incident on point a, or the device can be used both for excitation and detection. Acoustic excitation using the same device is described hereinafter whereby one part of the sample (point A 1902) is excited acoustically using an intense modulated laser beam such as a pump beam 1906, and another point on the sample is used to detect the acoustic response (point B 1904) using a less intense beam such as the probe beam 1908. If the pump beam 1906 is not an external source, but rather part of the modulated beam, then pump and probe beam intensities are controlled using a directional coupler splitting ratio. An optional waveguide amplifier can be used in the path of the pump beam 1906 to further amplify the pump beam intensity. A lens 1910 is used to focus both the pump and probe beams at the surface of the sample, and to collect light from the probe beam. To avoid leaking of the pump beam to the photo-detector 1912, and optional optical-isolator can be used in the path of the pump beam. The optical isolator can be either part of the waveguide device 1914, an external bulk-optic isolator or a fiber-optic isolator. A phase delay is inserted between the pump beam modulation and the modulated probe beam because of the time of travel of the acoustic waves from point A to point B through various paths. Amplitude data indicates the size of the subsurface or surface feature, or thickness of a subsurface layer, whereas the phase data indicates the location of the feature. Phase measurement also yields information about the material properties of the sample and material anomalies in the sample, such as density variation.

The architecture depicted in FIG. 19 can also be implemented using fiber-optic components, bulk optic components, or a combination. By varying the distance of point A and point B, various depth measurements can be performed. Position of point A and B can be controlled using the focusing lens 1910 and sample positions. If a fiber-based architecture is used, varying the distance between the two arms of the interferometer, where the pump and probe beams exit, changes the location of point A and B.

To increase the signal to noise ratio of detection in the various described detection schemes, a lock-in amplifier can be used.

The various described sensors can implement surface and subsurface detection using direct light modulation. To obtain information about small features in the nanometer scale, the pulsed laser is to have sufficiently wide bandwidth, generally in a range from 10 to 100 GHz, to yield information in the nanometer scale. Pulsed lasers suitable to achieve a suitable bandwidth are mode-locked lasers, which have picosecond to femtosecond pulse widths, a sufficient width for nano-scale interrogation. The lasers are typically expensive and would add complexity to the detection system.

To minimize cost and reduce the number of additional units, for example pulsed lasers, a method can be implemented that utilizes a continuous wave (CW) laser directly modulated or combined with a modulator. The technique can avoid usage of a mode-locked laser. The sensor can be modulated with a high-frequency signal (RF), which is used both for generating the acoustic signal, as well as down-converting the high-frequency acoustic signal to low-frequency electronic signal by mixing the acoustic and RF signals. Eliminating the use of a pulsed laser is more economic, consumes less power, and is more compact.

Theoretical assumptions of acoustic generation establish the limits for detection using direct modulation. An acoustic generation system can use either direct modulation of a CW laser or combined modulation of a pulsed laser such as a Q-switched laser and direction modulation. Various architectures can implement the acoustic generation system. The method can be combined with other techniques to attain higher-than-optical resolution detection and for metrology.

Figure 20:
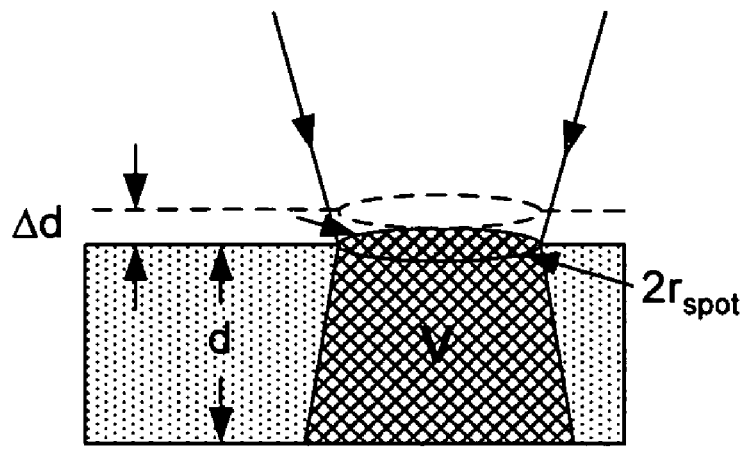
FIG. 20 is a cross-sectional view showing an example of measurement sample to illustrate an applicable theory of acoustic generation and detection.

Referring to FIG. 20, a cross-sectional view shows an example of measurement sample to illustrate an applicable theory of acoustic generation and detection. Several equations facilitate understanding of acoustic excitation energy specifications. FIG. 20 illustrates excitation and detection of an acoustic signature in a thin film for a layer thickness d and change in thickness Δd. Strain is given by equation (2) as follows:

$$\text{Strain} = \epsilon = \Delta d/d. \tag{2}$$

Strain energy per unit volume is given by equation (3), as follows:

$$\epsilon_V = (1/2) C_{11} \epsilon^2. \tag{3}$$

In an example arrangement, for purposes of explanation, some typical values can be entered. Layer thickness d can be 1 micron and Δd can be 1 nm, a value that can easily be detected with an interferometer. A suitable strain energy ε can be $10^{-3}$. $C_{11}$ can be $11 \times 10^{10}$ N/m$^2$ assuming the material is Aluminum and $\epsilon_V$ can be 0.5 $(11 \times 10^{10})$ $(10^{-3})^2$ $(5.5 \times 10^4$ N/m$^2$ or $5.5 \times 10^4$ J/m$^3$).

Assuming the laser light is focused to 2.5 micron diameter ($r_{spot}=1.25$ micron), and strained region is limited within the diameter, the volume of the area is given by equation (4) as follows:

$$V = \pi \cdot r^2_{spot} d, \tag{4}$$

so that for the illustrative example, the volume V is π (1.25× $10^{-6}$ m)$^2 \cdot (10^{-6}$ m) or $4.9 \times 10^{-18}$ m$^3$.

The energy to produce $\epsilon = 10^{-3}$ is given by equation (5), as follows:

$$E = \epsilon_V \cdot V = (5.5 \times 10^4 \text{ J/m}^3) * (4.9 \times 10^{-18} \text{ m}^3) = 0.3 \times 10^{-12}$$
$$\text{J} = 0.3 \text{ pJ}. \tag{5}$$

When using a mode-locked pulsed laser for acoustic excitation, losses typically occur. Assuming only 1% of the acoustic energy ($\eta_M = 0.01$) is converted to the desired mode to produce the depicted strain, the pulsed laser generates a broad frequency range, whereas the resonances are narrow band. Also, the material is not perfectly absorptive and generally only part of the light is absorbed. Assuming only 10% of light energy is transferred to acoustic energy ($\eta_L$=0.1), the pulsed laser energy to produce the strain is given by equation (6):

$$E_{pulse} = E/\eta_M \cdot \eta_L. \quad (6)$$

For the illustrative example, the laser pulse energy $E_{pulse}$ to produce the abovementioned strain is 0.3 nJ, the energy requirement for a mode-locked laser.

Figure 21:
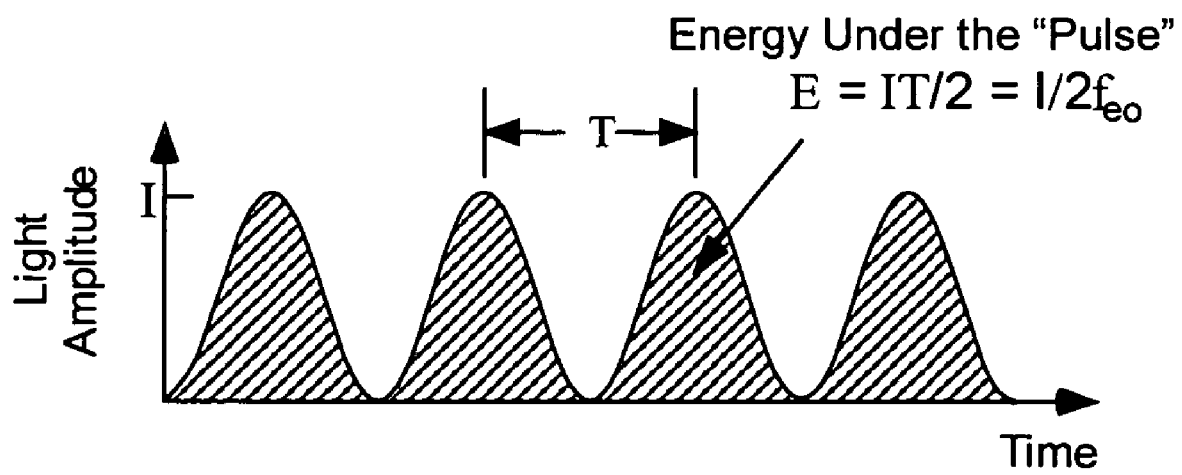
FIG. 21 is a time plot of modulated light amplitude and energy per period illustrating modulation of a continuous laser as an acoustic source.

The illustrative sensors can implement various acoustic excitation schemes. For example, referring to FIG. 21, a time plot of modulated light amplitude and energy per period is shown to illustrate modulation of a continuous laser as an acoustic source. Assuming that instead of using a pulsed laser, the acoustic signal is generated by modulating a continuous wave (CW) laser with a sinusoidal signal as shown in FIG. 21, at frequency $f_{eo}$. For example the acoustic signal can be generated using direct modulation and external modulation such as an electro-optic modulator or an electro-absorptive modulator.

If the modulator is biased such the signal modulates from 0 to I, the maximum light intensity, then the energy under each period is depicted in equation (7):

$$E_{eo} = I \cdot T/2 = I \cdot (\frac{1}{2} f_{eo}). \quad (7)$$

Assuming losses due to absorption $\eta_L$, loss due to conversion to acoustic mode is $\eta_M$. Therefore energy to produce the abovementioned strain is calculated using equation (8):

$$E_{acst-eo} = E_{eo} \cdot \eta_M \cdot \eta_L = (\eta_M \cdot \eta_L) \cdot I \cdot (\frac{1}{2} f_{eo}). \quad (8)$$

For an example arrangement, typical values can be I equal to 10 mW, $f_{eo}$ of 50 GHz, and $E_{eo}$ equal to 0.1 pJ. Assuming most energy is converted to acoustic energy at that frequency $f_{eo}$ for example a resonant effect, then $\eta_M$=1. If the optical absorption is 50%, and $\eta_M$ is 0.5, then $E_{acst-eo}$ is 0.05 pJ, an order of magnitude smaller than the energy given in equation (5). To overcome the energy specification, a higher power light can be used. If light is amplified, for example using an Erbium doped fiber amplifier (EDFA), then energy transferred to acoustic energy will be higher. For example, if light intensity I is 100 mW, then $E_{acst-eo}$ is 0.5 pJ, a level that satisfies the energy requirement to produce $\epsilon$ is $10^{-3}$ given in equations (2) to (5). Further amplification for I equal to 1 W produces $E_{acst-eo}$ of 5 pJ, which is one order of magnitude higher than the required energy to produce $\epsilon$ equal to $10^{-3}$.

Additionally, the interferometer can measure displacements much smaller than 1 nm and thus can detect smaller strain, therefore the energy requirements can be further relaxed, possibly making light amplification unnecessary.

Figure 22:
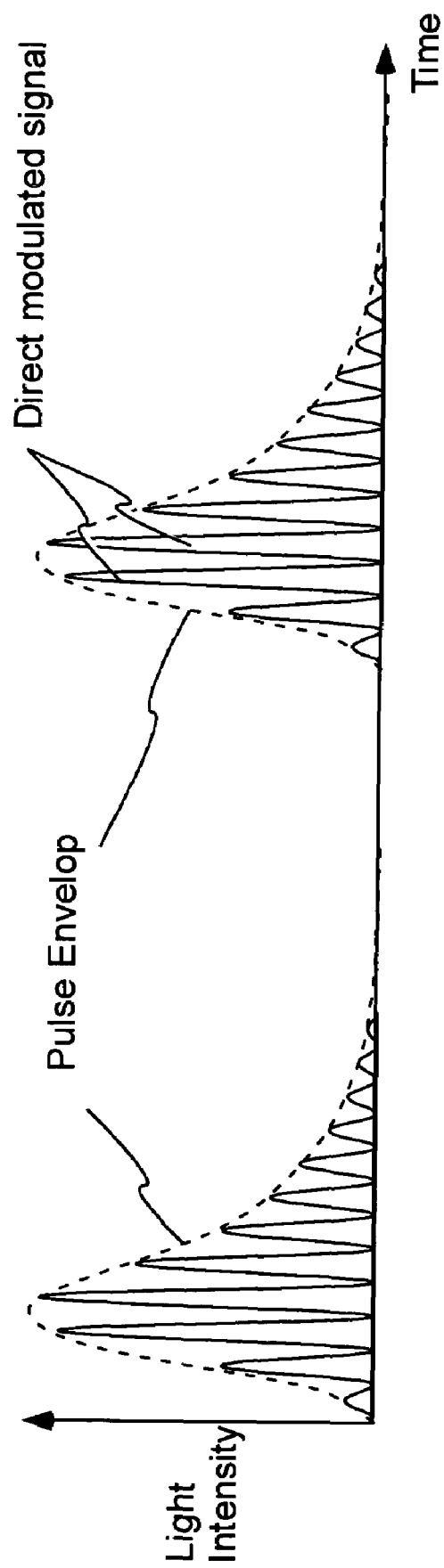
FIG. 22 is a time plot of light intensity showing light intensity output when combining pulse light output, for example using a Q-switched laser or a pulsed diode laser, with direct light modulation.

In another acoustic excitation scheme, a pulsed laser can be combined with an external modulator. Referring to FIG. 22, a time plot of light intensity shows light intensity output when combining pulse light output, for example using a Q-switched laser or a pulsed diode laser, with direct light modulation. A sufficiently high enough acoustic energy can be attained by combining a pulse modulated laser with a direct modulation, for example with an external modulator. In the illustrative arrangement, the pulsed laser is not a mode-locked laser which produces very high peak powers but is generally expensive, but instead is either a Q-switched laser or a simple laser diode that can be pulsed to produce high peak powers in a short period of time. Generally, if used alone, Q-switched or direct pulse-modulated lasers do not have suitable bandwidth to produce acoustic frequencies of interest. For example, a Q-switched laser with 10 ns pulse width produces acoustic frequencies up to 100 MHz. To interrogate features in the nanometer size range, frequencies should be higher than 10 GHz. Therefore simply using a Q-switched or a direct pulse-modulated diode laser is not typically sufficient, although combination with a high-frequency modulation scheme can result in a sufficiently high peak power and suitable bandwidth to interrogate features at nanometer resolution. FIG. 22 illustrates results of a suitable arrangement, where the dashed envelop is the laser pulse envelope and higher oscillations result from high-frequency external modulation.

In the illustrative configuration $E_{eo}$ is much higher than a for a CW laser, therefore $E_{acst-eo}$ is also much higher. For example, a pulse-modulated diode laser can produce peak powers of I equal to 100 W, thus resulting in $E_{acst-eo}$ of 500 pJ which is sufficiently high energy compared to the required minimum energy of 0.3 pJ to produce $\epsilon$ of $10^{-3}$ as described according to the described theory of acoustic generation and detection.

Various sensor architectures can be used to attain surface and subsurface detection with direct light modulation. For example, referring to FIG. 23, a schematic pictorial and block diagram illustrates an embodiment of a cascaded interferometric architecture 2300 with modulated laser beams used as acoustic excitation or pump source. The illustrative interferometer 2300 includes a band pass filter 2302 and a photo detector 2304. Photo detectors 2304 can be a single element detector, a linear array, or a two-dimensional array such as a camera. The illustrative interferometer 2300 also is shown with an erbium doped optical amplifier 2306 which is optional and can be replaced with any suitable optical amplifier. Modulators 2308 and 2310 can also be combined into the same modulator for homodyne detection.

Figure 24:
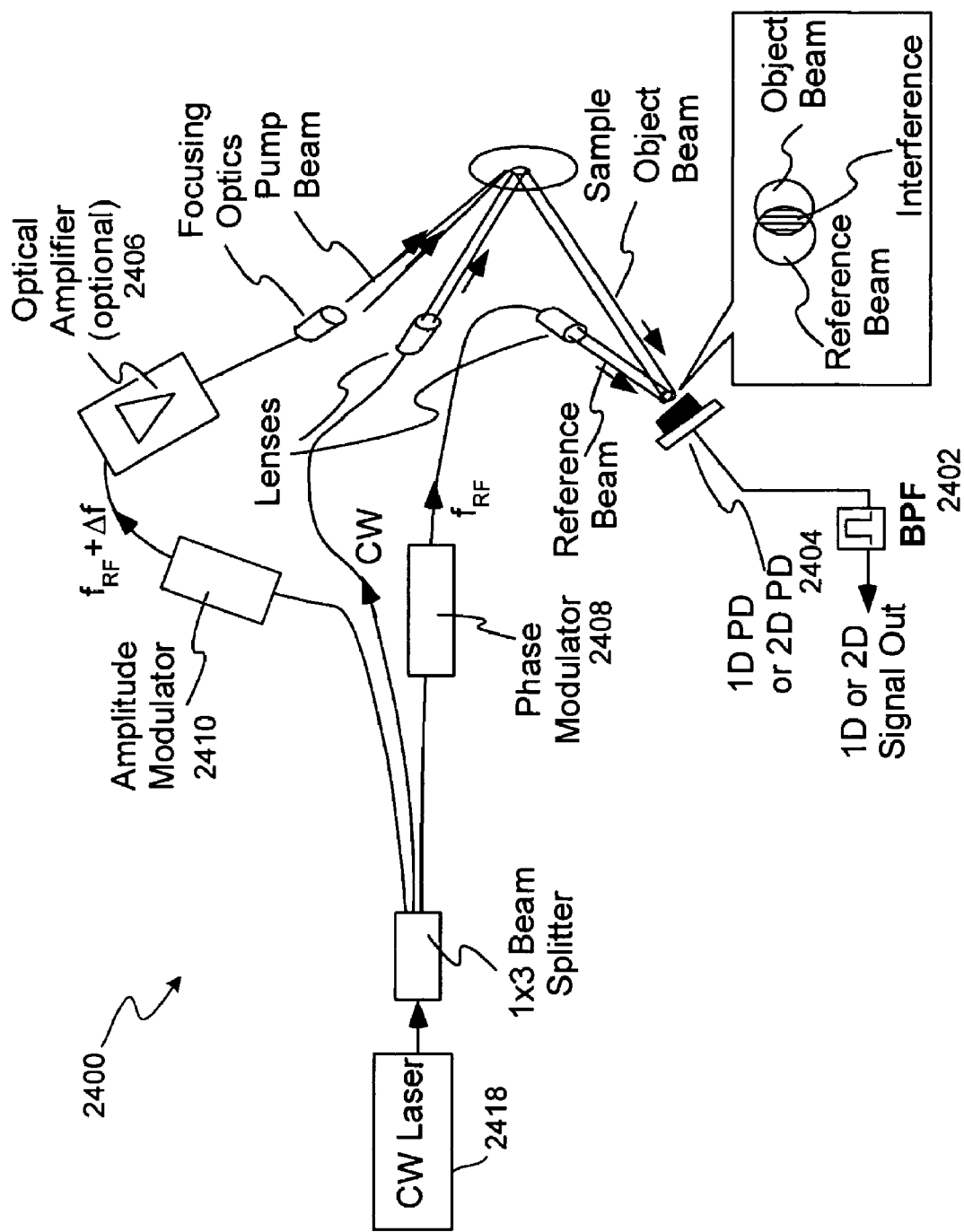
FIG. 24 is a schematic pictorial and block diagram that illustrates an embodiment of a cascaded interferometric architecture with modulated laser beams used as acoustic excitation or pump source and a single modulator used for homodyne detection.

Referring to FIG. 24, a schematic pictorial and block diagram illustrates an embodiment of a cascaded interferometric architecture 2400 with modulated laser beams used as acoustic excitation or pump source. The illustrative interferometer 2400 includes a band pass filter 2402 and a photo detector 2404. Photo detectors 2404 can be a single element detector, a linear array, or a two-dimensional array such as a camera. The illustrative interferometer 2400 also is shown with an erbium doped optical amplifier 2406 which is optional and can be replaced with any suitable optical amplifier. Modulators 2408 and 2410 can also be the same modulator for homodyne detection.

FIG. 24 depicts an architecture that can result in simultaneous two-dimensional interrogation and imaging. The modulated laser beam is also used as an acoustic excitation source. Light is split into two parts either using a reflective optics or fiber couplers, such as a 1×2 optical splitter. One part of the light, a probe beam, is directed towards the interferometer. Another part is sent to an optional optical amplifier 2406. The amplified light is then used as an acoustic excitation source as a pump beam. If a fiber amplifier is used such as an Erbium doped fiber amplifier (EDFA), then both the probe and the pump beams have the same wavelength. To eliminate noise generated by the pump beam leakage to camera 2404, the two beams can be spatially separated so that the probe beam does not reach the camera 2404. To further reduce noise, an optional acousto-optic (AO) modulator 2410 can be used to produce a shifted modulation frequency. The detected signal can then be passed through a band-pass filter (BPF) 2402 or a lock-in amplifier tuned to detect the difference frequency ($\Delta f$). The sensing scheme can detect the difference frequency between the optical and acoustic signals. If the CW laser 2418 is modulated at $f_{RF}$ then the probe beam is modulated at $f_{RF}$, whereas the pump beam is modulated at $f_{RF}+\Delta f$, where $\Delta f$ is due the second modulator, for example AO modulation.

Figure 25:
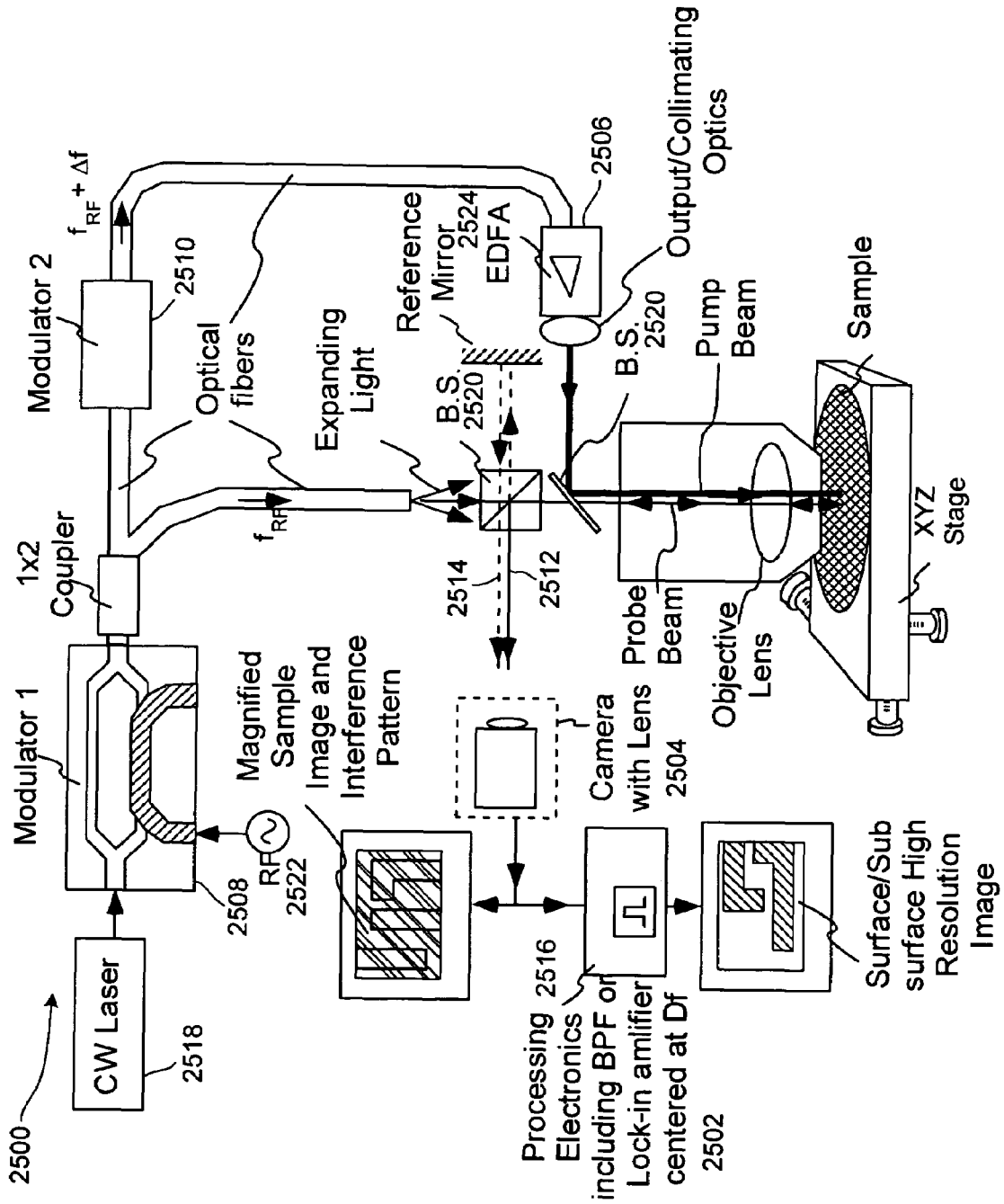
FIG. 25 is a schematic pictorial and block diagram that illustrates another embodiment of a cascaded interferometric architecture.

Tuning a band pass filter 2502 or lock-in amplifier to pass $\Delta f$ enables detection of signal that is due to the pump laser generated acoustic signal and the response of the sample is shown in FIG. 25. Pump and probe light can be generated from different light sources and not necessarily the same laser. Referring to FIG. 25, a schematic pictorial and block diagram illustrates an embodiment of a cascaded interferometric architecture 2500 with modulated laser beams used as acoustic excitation or pump source. Solid and dashed lines illustrate reference 2512 and object 2514 light paths (the optic axis), respectively. Processing electronics 2516 include band pass filtering and/or lock-in amplification, image subtraction, convolution, correlation, Fourier transform and image processing algorithms. The illustrative interferometer 2500 includes a band pass filter 2502 and a photo detector 2504. A photo detector 2504 is depicted as a two-dimensional array such as a camera. The illustrative interferometer 2500 also is shown with an erbium doped optical amplifier 2506 which is optional and can be replaced with any suitable optical amplifier. The interferometer 2500 further is shown with a continuous wave (CW) laser 2518, a beam splitter 2520, and a radio frequency (RF) modulation signal generator 2522. Modulator 2508 is an integrated Mach-Zehnder modulator with electrodes shown hatched, and waveguides clear, but can otherwise be direct modulated laser, an electro-absorption modulator, or any other means to modulate the CW laser light. Modulator 2510 can be an acousto-optic modulator, an electro-optic modulator, a direct modulated laser modulating at $f_{RF}+\Delta f$, or any other means of light modulation. Prisms and optical components can be added between the beam splitter 2520 and reference mirror 2524 to attain optical delay at a shorter distance or to match the wavefronts of the probe and reference beams. Modulators 2508 and 2510 can also be combined into the same modulator for homodyne detection ($\Delta f=0$). Pump and probe light can be generated from different light sources, but may be produced by the same laser.

Figure 23:
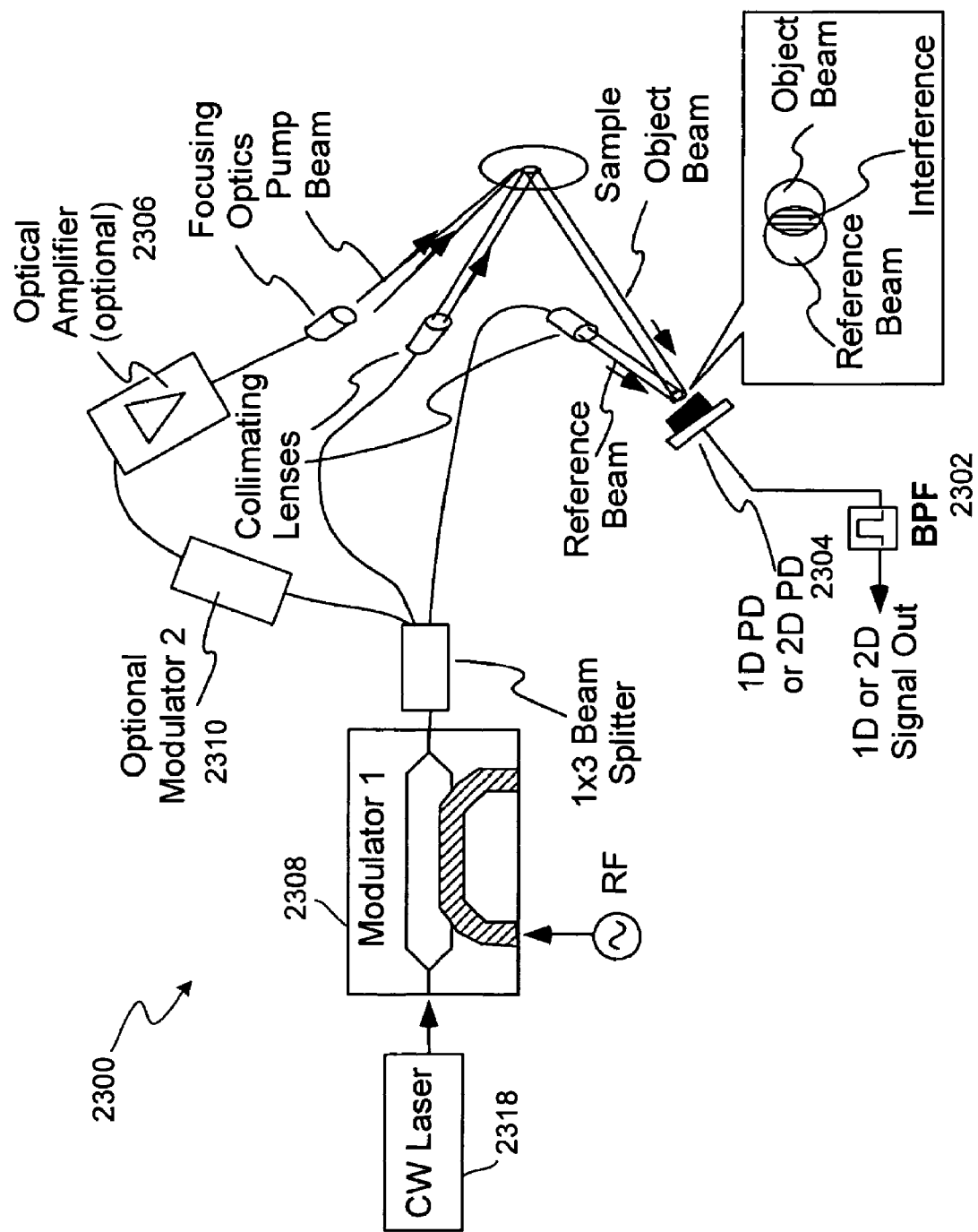
FIG. 23 is a schematic pictorial and block diagram that illustrates an embodiment of a cascaded interferometric architecture with modulated laser beams used as acoustic excitation or pump source.

Various architectures that can be utilized using direct modulation with an optical amplifier, or using a combination of pulsed laser, for example Q-switched or a pulse-modulated diode laser, with an external modulator as shown in FIGS. 23, 24, and 25. For clarity, the illustrations only show a continuous wave (CW) laser with modulator and amplifier. In the case of pulsed/external modulated scheme, the CW laser can be replaced with the pulsed laser, particularly in the pump beam path. In various embodiments, the pulsed laser beam, for example a mode-locked laser beam, can be replaced with a light path that contains a second modulator.

In the architectures shown in FIGS. 23, 24, and 25, both modulators can be combined so that the same modulator used for both pump and probe beams for homodyne detection ($\Delta f=0$).

The schemes shown in FIGS. 23, 24, and 25 illustrate acoustic generation without using a mode-locked laser, a scheme that is not limited to the illustrated architectures alone, and is applicable to all the architectures described herein.

Furthermore, FIGS. 23, 24, and 25 illustrate use of optical fibers. The same structures and techniques can be implemented using free-space optical architectures, where either bulk optics are used instead of optical fiber components, or both fiber and bulk optical components are combined.

To increase signal-to-noise ratio of detection in the illustrative structures and techniques, a lock-in amplifier can be used.

In some embodiments, a sensor may combine various acoustic excitation methods with different sensor architectures. The disclosed sensors and sensing techniques for exciting acoustic waves using continuous wave laser modulation, or by combining pulsed lasers with an external modulator can be used with various other sensing techniques and architectures for several purposes. In some configurations, acoustic excitation can be used to produce higher-than optical resolution data. In some arrangements acoustic excitation can be used for surface and subsurface detection, metrology applications, anisotropic measurements, or other applications. The structures and techniques can also be used to perform a combination of applications. Polarization optics can also be used to further increase signal-to-noise ratio and enhance the functionality of this system. In addition, the methods can be combined with multiple modulator approach which is described hereinafter.

In some configurations, a sensor can perform high frequency modulation using multiple cascaded or parallel modulators and lasers. To attain high resolution surface and sub-surface interrogation using the described acoustic spectrum analyzer architectures high-frequency modulation can be used. Spatial depth resolution is directly proportional to frequency of modulation.

One method of achieving high frequency modulation is to use devices with ultra-high frequency response, for example up to 100 GHz modulation. However, such devices are often expensive and hard to fabricate. More economical or technologically feasible configurations combine a multiple lower frequency modulation device to produce a combined higher frequency response. Several methods can be used to attain high frequency modulation using multiple low frequency components. One method includes serially cascaded modulators, another uses multiple modulators.

High-frequency modulation can be used for the probe beam and can also be used as a pump beam when the intensity is sufficiently large to produce the desired acoustic excitation.

Figure 26:
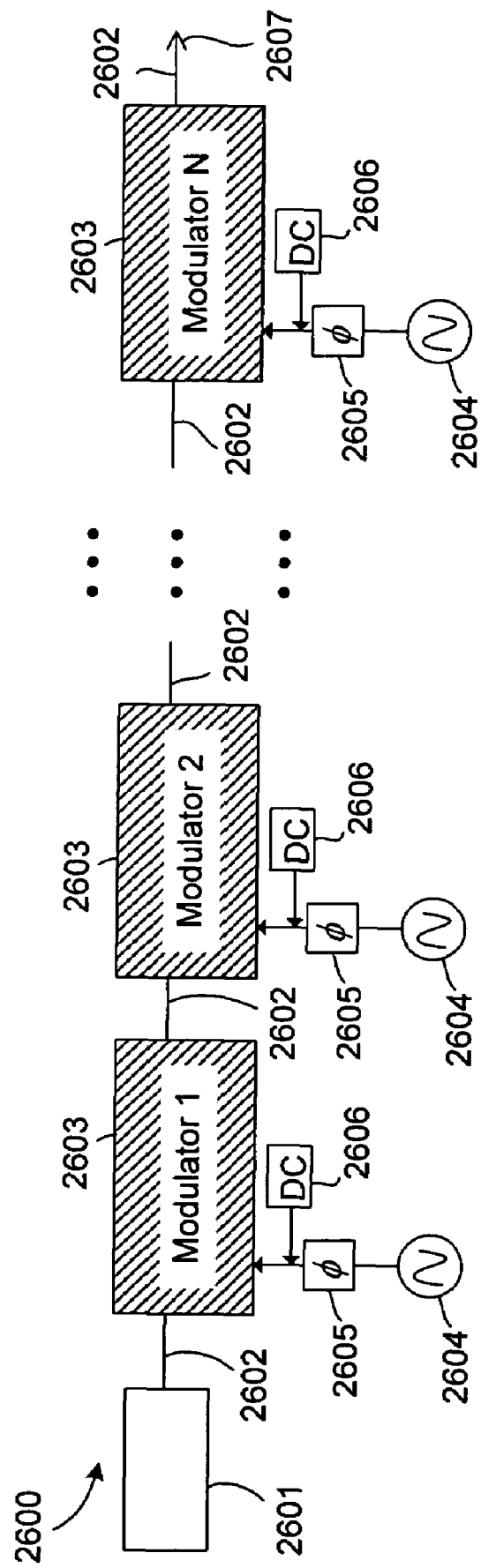
FIG. 26 is a schematic block diagram showing a serial modulator scheme that supplies high-frequency modulation using cascaded modulators.

Referring to FIG. 26, a schematic block diagram illustrates a serial modulator scheme that supplies high-frequency modulation using cascaded modulators. The illustrative serial modulator scheme 2600 comprises a laser 2601, optical fibers 2602, and a plurality (1–N) of cascaded optical amplitude modulators 2603 for an arbitrary number N modulators. The serial modulator 2600 further comprises a radio-frequency (RF) modulation signal generator 2604 with electrical phase shifters 2605 and DC bias generators 2606. The modulation signal generator 2604 can be supplied from the same source or separate sources. For maximum control, each modulator phase and DC bias are controlled independently. DC bias is attained either by combining the modulation signal with a DC voltage using a bias-Tee which is not shown in the figure to promote clarity, or by applying the DC voltage to a biasing electrode that is common to most optical modulators. The serial modulator 2600 can also include a modulated light output generator 2607.

The modulated light output generator 2607 supplies light that can be used as a probe beam and/or a pump beam if the intensity is sufficiently high for acoustic excitation, and can be used in the illustrative cascaded sensor configuration.

The cascaded modulator scheme depicted in FIG. 26 shows connections via optical fibers 2602. The same scheme can also be implemented using bulk-optic modulators with free space laser beam path as well as using an all-integrated optical modulator chip, incorporating modulators and couplers all on the same chip. The integrated scheme results in a more compact system than using fiber coupled or bulk-optic modulators.

The response of the individual amplitude modulators 2603 is given by equation (9) as follows:

$$P_o = \frac{T_D P_{in}}{2}\{1 + \cos[\theta + \Delta\phi]\} \qquad (9)$$

where θ is the DC bias for example π/2 for quadrature bias, $P_{in}$ is the input light intensity, $T_D$ represents optical losses through the modulator, and Δφ is given by equation (10):

$$\Delta\phi = X\sin(\omega t - \phi) \qquad (10)$$

where ω=2πf and f is the modulation frequency, t is time, φ is the electrical phase shift of the modulation signal, and X is the response of the modulator to the electrical modulation signal. For a single modulator, therefore the output signal is given by equation (11):

$$P_o = \frac{T_D P_{in}}{2}\{1 + \cos[\theta + X\sin(\omega t - \phi)]\}. \qquad (11)$$

When modulators are cascaded as shown in FIG. 26, the output signal using N modulators is found by multiplying the response of each modulator, as depicted in equation (12):

$$P_{tot} = P_{in} \prod_{i=1}^{N} \left(\frac{T_{D_i}}{2}\right)\{1 + \cos[\theta_i + X_i\sin(\omega_i t - \phi_i)]\} \qquad (12)$$

where subscript i denotes the corresponding parameter for the ith modulator.

The proper control of electrical phase and modulator bias can yield high frequency generation using lower frequency modulators. For example, if all the modulators are modulated at the same frequency, namely $\omega_1=\omega_2=\ldots=\omega_N$, all modulators biased at quadrature ($\theta_i=\pi/2$), and modulation drive signal phase set to $\phi_i=(i-1)(2\pi/N)$, then the modulated output will have a large modulation component at frequency Nω.

Figure 27:
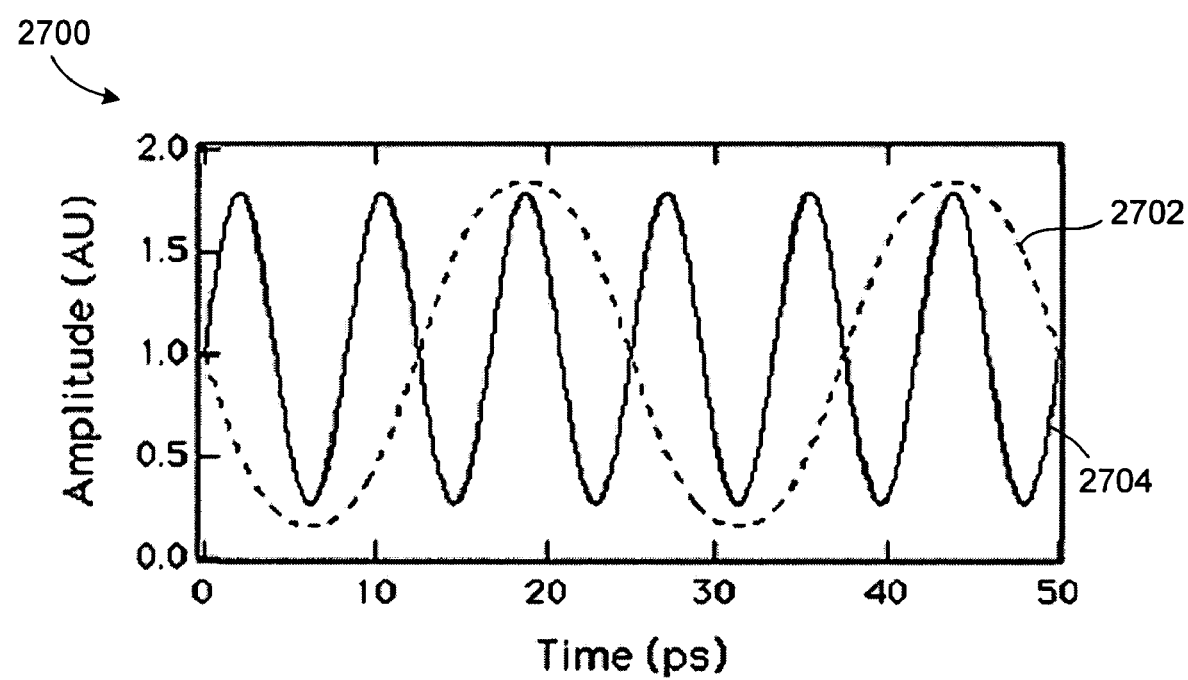
FIG. 27 is a graph showing an example output signal from the modulators in a simulation.

For example, using three modulators (N=3), and setting $\omega=\omega_1=\omega_2=\omega_3$ and setting modulators at quadrature, i.e. $\theta_1=\theta_2=\theta_3=\pi/2$, and $\phi_1=0$, $\phi_2=2\pi/3$ and $\phi_3=4\pi/3$, the output of the three modulators results in a modulated output of 3ω. FIG. 27 is a graph showing an example output signal from the modulators in a simulation at frequency f=40 GHz. The illustrative modulation simulation 2700 uses three cascaded amplitude modulators each modulated at frequencies f=40 GHz (period=25 ps). A dotted line 2702 indicates light intensity modulation using a single modulation. A solid line 2704 shows light intensity modulation at the output of three cascaded modulators, each modulated at f=40 GHz, with bias set to quadrature (i.e. $\theta_1=\theta_2=\theta_3=\pi/2$), and $\phi_1=0$, $\phi_2=2\pi/3$ and $\theta_3=4\pi/3$. In the example simulation, the three 40 GHz cascaded amplitude modulators result in 120 GHz modulation (period=8.3 ps).

Figure 28:
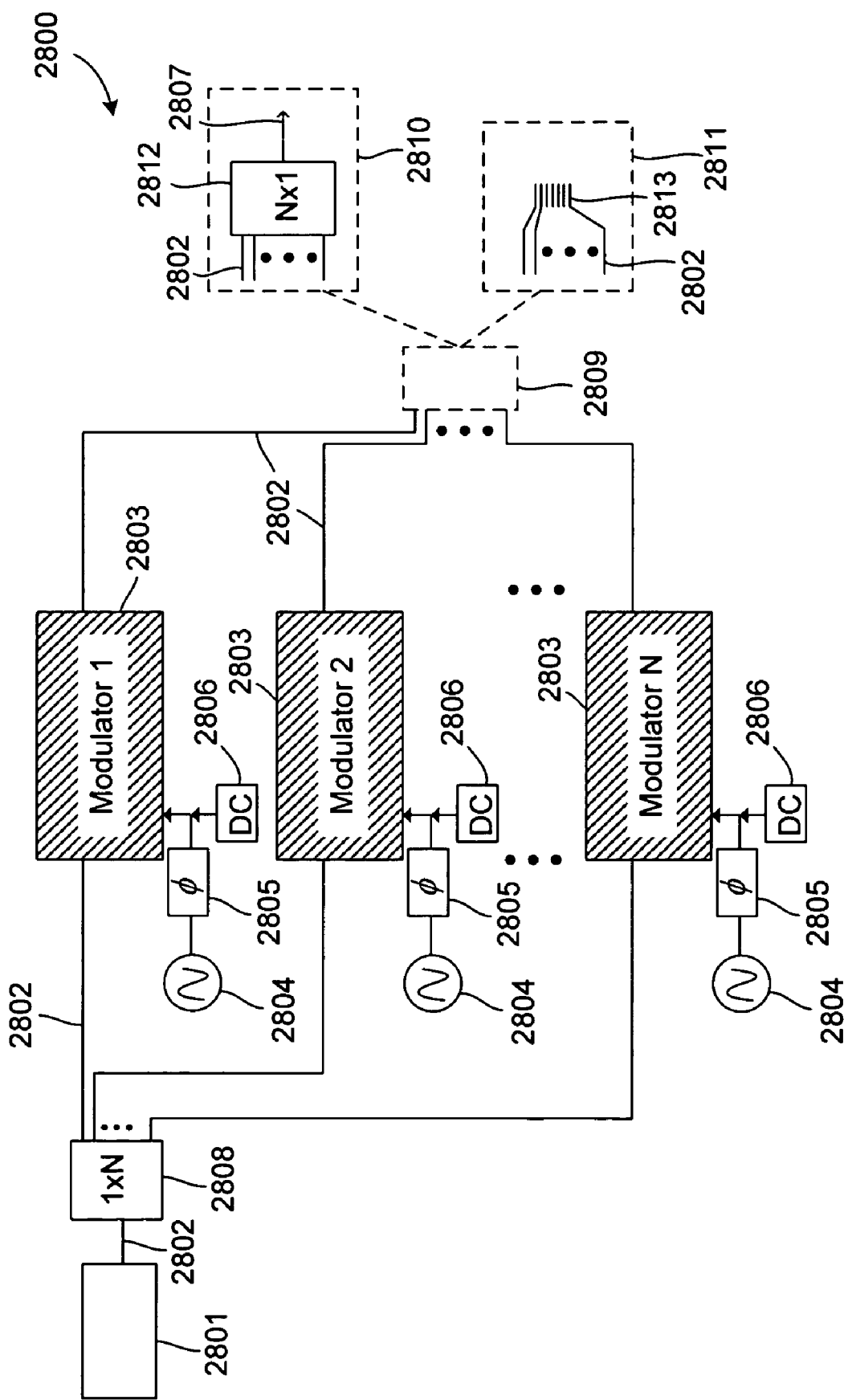
FIG. 28 is a schematic block diagram illustrating an embodiment of a high-frequency modulation structure including parallel amplitude modulators with mutually coherent light.

Referring to FIG. 28, a schematic block diagram illustrates an embodiment of a high-frequency modulation structure 2800 including parallel amplitude modulators 2803 with mutually coherent light. High frequency modulation can be achieved using N parallel amplitude modulators 2803. Multiple light paths are produced from a mutually coherent light beam, such as from a single laser 2801. The illustrative parallel modulator scheme 2800 comprises a laser 2801, optical fibers 2802, and a plurality (1–N) of parallel optical amplitude modulators 2803 for an arbitrary number N modulators. The parallel modulator 2800 further comprises a radio-frequency (RF) modulation signal generator 2804 with electrical phase shifters 2805 and DC bias generators 2806, and a modulated light output generator 2807. Laser light is split into N outputs via 1×N fiber coupler 2808, fed into N modulators where N is an arbitrary number, and recombined again 2809 either using another fiber coupler 2810, for example using an N×1 fiber coupler 2812, or by using a fiber bundle scheme 2811, such as using a fiber ribbon 2813. The fiber coupled scheme 2810 is suitable both for fiber based interferometers, where a fiber collimator is used in the probe beam path, and/or bulk optic interferometer based setups, and is therefore a more general approach. Fiber bundle based scheme 2811 is more suitable for the bulk optic interferometer based setup.

The illustrative configuration can also be implemented using bulk optics, where fiber-couplers 2808 and 2812 are replaced by reflective or diffractive (such as grating based) beam splitters. The structure 2800 can also be integrated on a single electro-optic chip, where light routing is achieved using optical waveguides, Y junction and/or directional coupler type beam splitters and combiners.

When coherent light source is used, and the various optical path lengths are much shorter than the optical coherence length of the light source, then light can be added coherently, which can be calculated using equation (13):

$$P_{tot} = P_{in} \left|\sum_{i=1}^{N} \exp(i\Delta\phi_i) + \exp(i\theta_i)\right|^2 \qquad (13)$$

where Δφ is given by equation (10), and θ is the DC bias of the modulator (for example π/2 for quadrature bias). Subscript i denotes a corresponding parameter for the ith modulator. Amplitude factors such as losses due to fiber splitters, fiber couplers, and other optical system losses can be added to the equation (13) as a multiplying factor to the corresponding ith exponent to obtain exact modulation amplitude. The factors are set to 1 in equation (13) to facilitate clarity.

Figure 29:
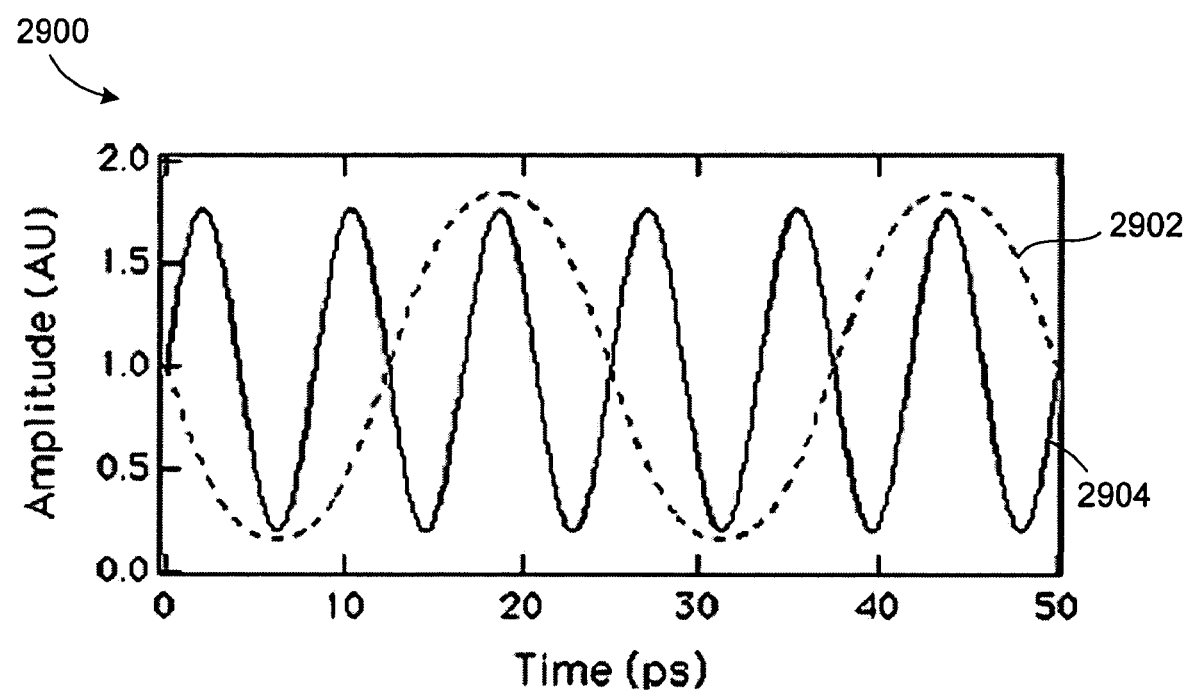
FIG. 29 is an amplitude graph depicting a three modulator simulation.

Suitable control of electrical and optical can yield high frequency generation using lower frequency modulators. For example, if all the modulators are modulated at the same frequency, for example $\omega_1=\omega_2=\ldots=\omega_N$, if modulators biased at quadrature ($\theta_i=\pi/2$), and if modulation drive signal phase set to $\phi_i=(i-1)(2\pi/N)$, then the modulated output will have a large modulation component at frequency Nω. Referring to FIG. 29, an amplitude graph shows a three modulator simulation. The illustrative modulation simulation 2900 uses three parallel amplitude modulators and mutually coherent light beams each modulated at frequencies f=40 GHz (period=25 ps). Dotted line 2902 indicates light intensity modulation using a single modulation. Solid line 2904 is light intensity modulation at the output of three parallel modulators, each modulated at f=40 GHz, with bias set to quadrature (i.e. $\theta_1=\theta_2=\theta_3=\pi/2$), and $\phi_1=0$, $\phi_2=2\pi/3$ and $\phi_3=4\pi/3$. Use of three 40 GHz parallel amplitude modulators with a mutually coherent beams results in 120 GHz modulation (period=8.3 ps).

Figure 30A:
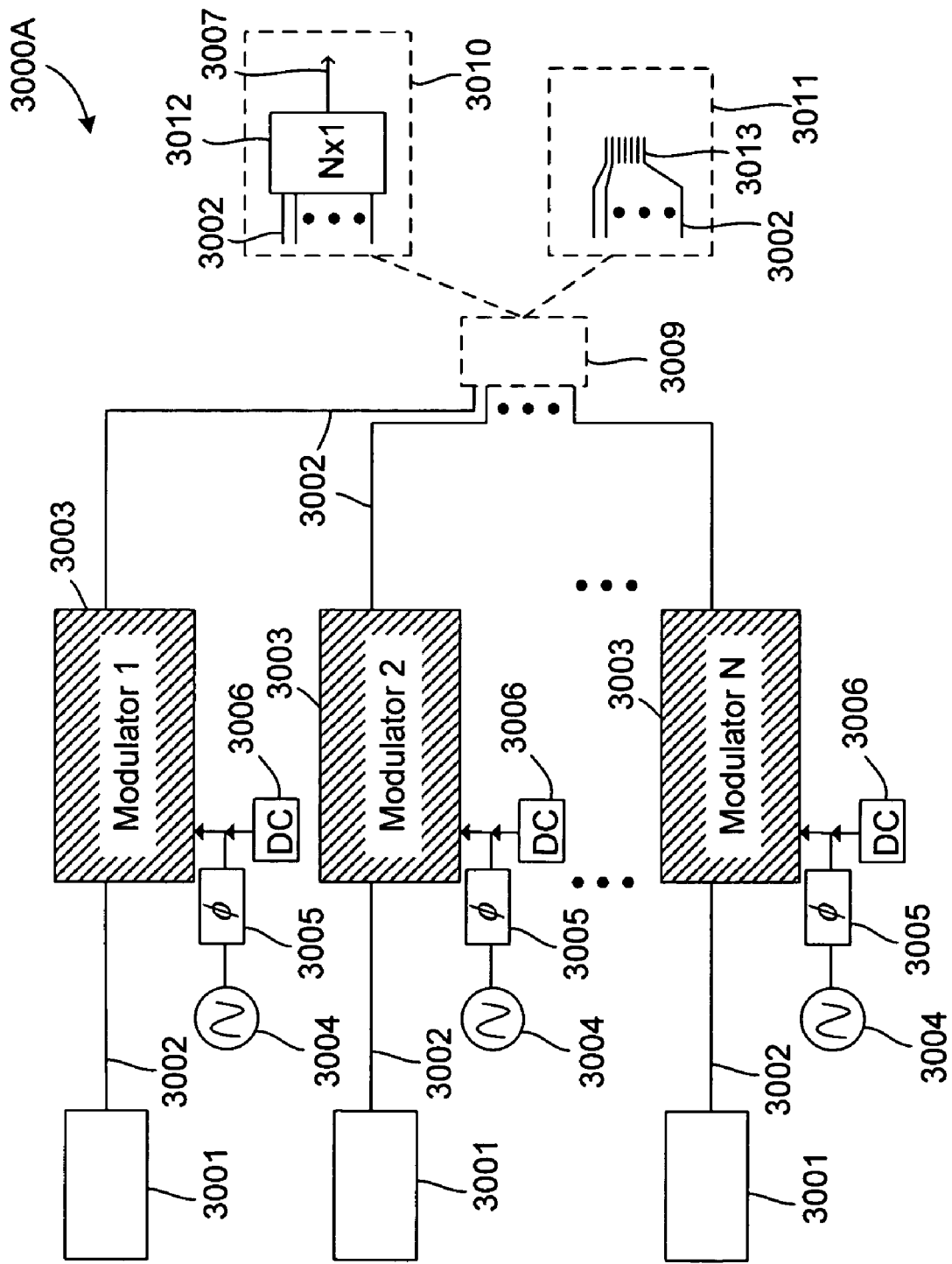
FIGS. 30A and 30B are schematic block diagrams that show embodiments of a high-frequency modulation structure including parallel amplitude modulators with mutually incoherent light.
Figure 30B:
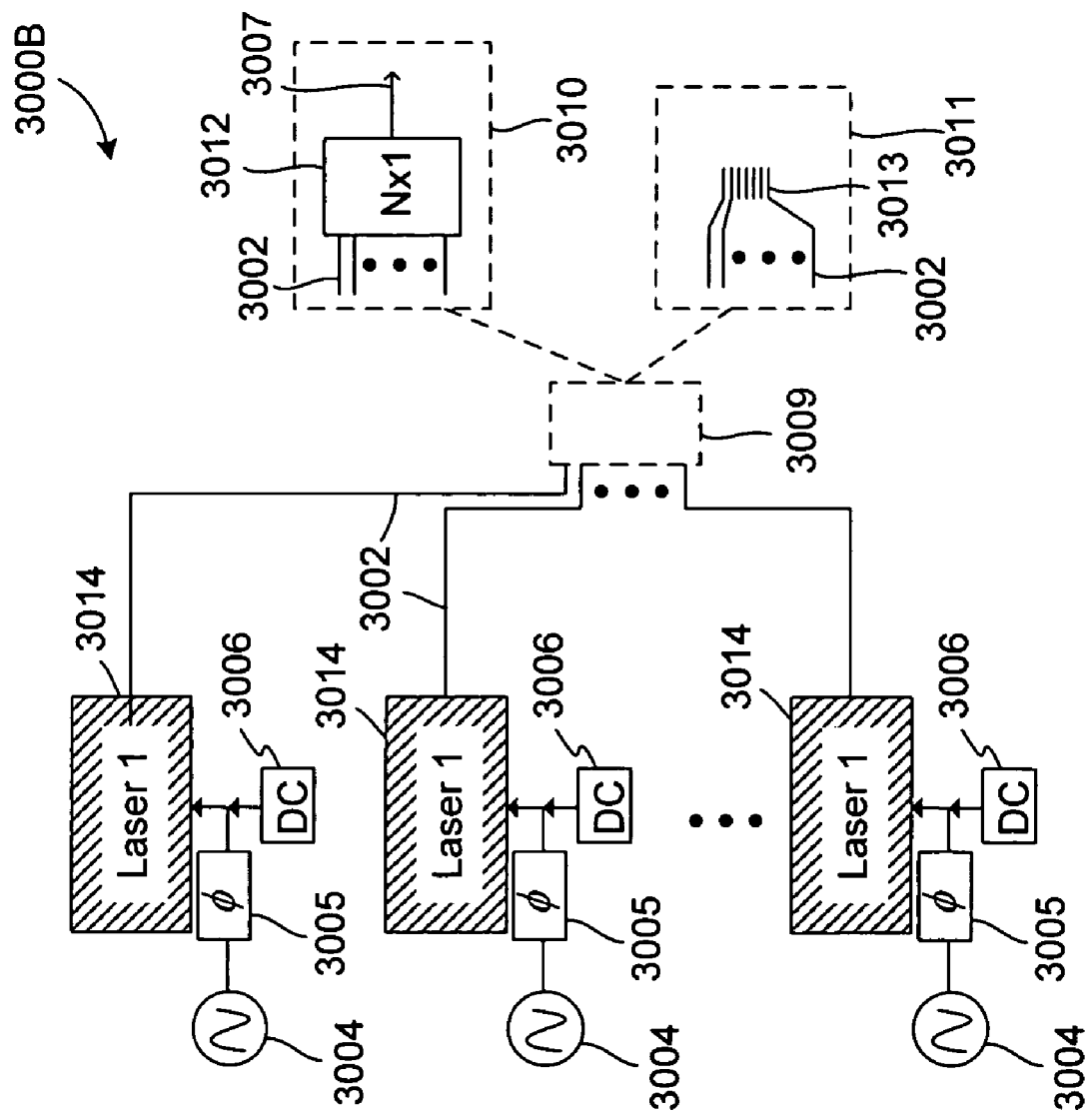

Referring to FIGS. 30A and 30B, schematic block diagrams illustrate embodiments of a high-frequency modulation structure 3000 including parallel amplitude modulators with mutually incoherent light. High frequency modulation can be attained using N parallel amplitude modulators using mutually incoherent beams as depicted in FIG. 30A, or N parallel direct modulated lasers as depicted in FIG. 30B.

The illustrative parallel modulator scheme 3000 using N mutually incoherent light sources 3001 comprises lasers 3001, optical fibers 3002, and a plurality (1–N) of parallel optical amplitude modulators 3003 for an arbitrary number N modulators. The parallel modulators 3000 further comprise a radio-frequency (RF) modulation signal generator 3004 with electrical phase shifters 3005 and DC bias generators 3006, and a modulated light output generator 3007. Laser light is split into N outputs via 1×N fiber coupler 3008, fed into N modulators where N is an arbitrary number, and recombined again 3009 either using another fiber coupler 3010, for example using an N×1 fiber coupler 3012, or by using a fiber bundle scheme 3011.

FIG. 30A shows a modulator 3000A with mutually incoherent light sources 3001 either coming from different light sources, or from the same light source with low coherence length. FIG. 30B uses a parallel laser to generate higher frequency than using a single modulated laser.

The configurations shown in FIGS. 30A and 30B can also be implemented using bulk optics, where fiber couplers 3012 are replaced by reflective or diffractive such as grating-based beam splitters. The arrangements can also be integrated on a single electro-optic chip, where light routing is achieved using optical waveguides, Y junction and/or directional coupler type beam splitters and combiners.

Operation of the parallel configurations can be described by equation (14):

$$P_{tot} = P_{in} \sum_{i=1}^{N} A_i \{1 + \cos[\theta_i + X_i \sin(\omega_i t - \phi_i)]\} \quad (14)$$

where $A_i$ is an amplitude factor of each light path, and is directly proportional to laser power and loss in the ith optical path. The other parameters are defined in equations described hereinbefore.

Proper control of electrical and modulator bias can yield high frequency generation using lower frequency modulators. For example, if all the modulators are modulated at the same frequency, namely $\omega_1 = \omega_2 = \ldots = \omega_N$, modulator bias set to quadrature ($\theta_1 = \pi/2$), and if modulation drive signal phase set to $\phi_i = (i-1)(2\pi/N)$, then the modulated output will have a large modulation component at frequency $N\omega$. A three modulation simulator simulation is depicted by a graph in FIG. 31.

Figure 31:
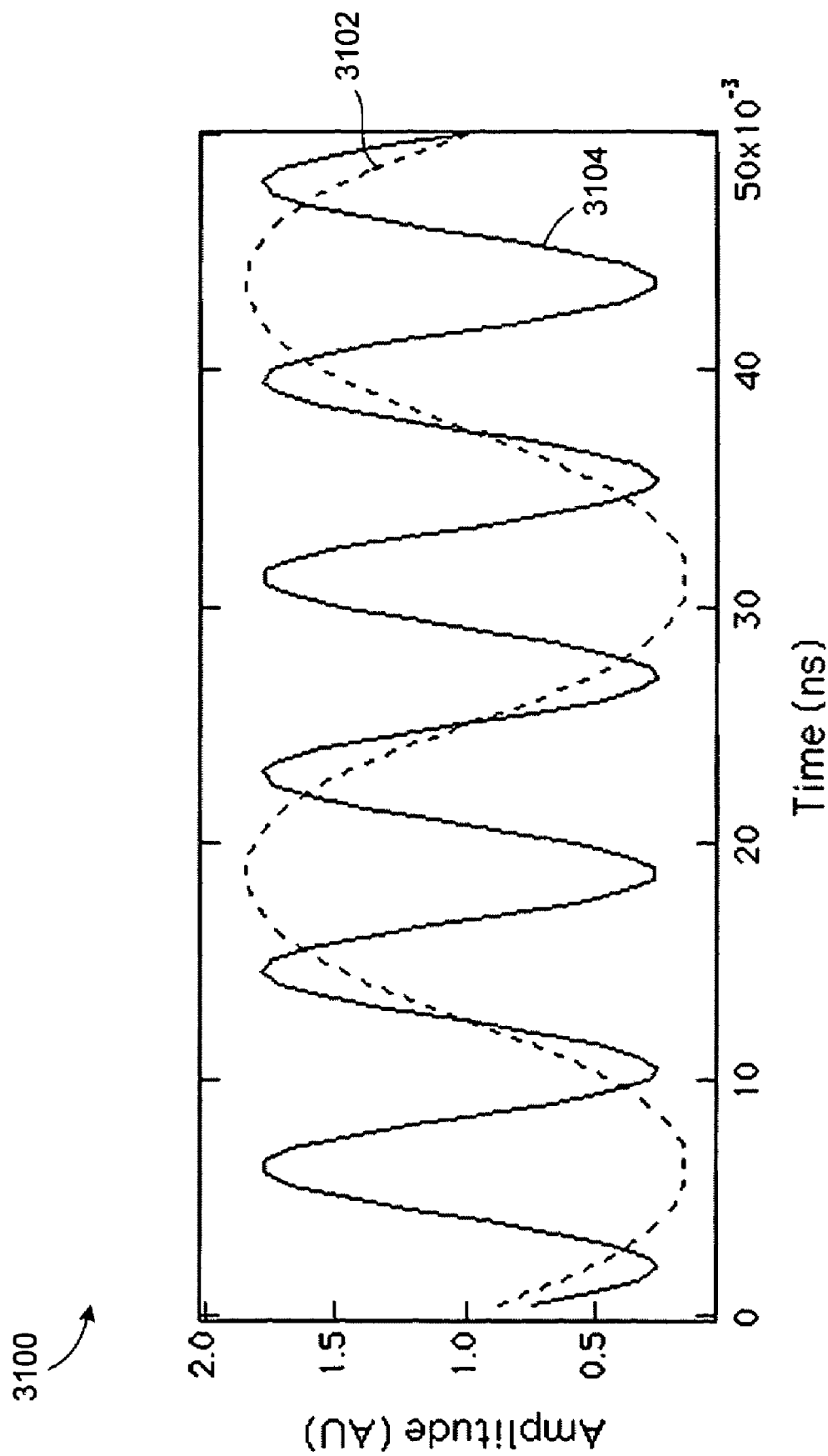
FIG. 31 is an amplitude time plot depicting a modulation simulation 3100 using three parallel modulators and mutually incoherent light beams.

Referring to FIG. 31, an amplitude time plot shows a modulation simulation 3100 using three parallel modulators and mutually incoherent light beams each modulated at frequencies f=40 GHz (period=25 ps). Dotted line 3102 indicates light intensity modulation using a single modulation. Solid line 3104 is light intensity modulation at the output of three parallel modulators, each modulated at f=40 GHz, with bias set to quadrature (i.e. $\theta_1 = \theta_2 = \theta_3 = \pi/2$), and $\phi_1 = 0$, $\phi_2 = 2\pi/3$ and $\phi_3 = 4\pi/3$.

The arrangements depicted in FIGS. 30A and 30B use mutually incoherent light and are therefore suitable for applications where interferometric detection is not necessary. One such application is the acoustic spectrum analyzer system described hereinbefore to generate a high frequency modulated pump beam for acoustic excitation. The sensor and associated method yield higher frequency and higher optical power using multiple modulated lasers than using a single modulated laser.

Figure 32:
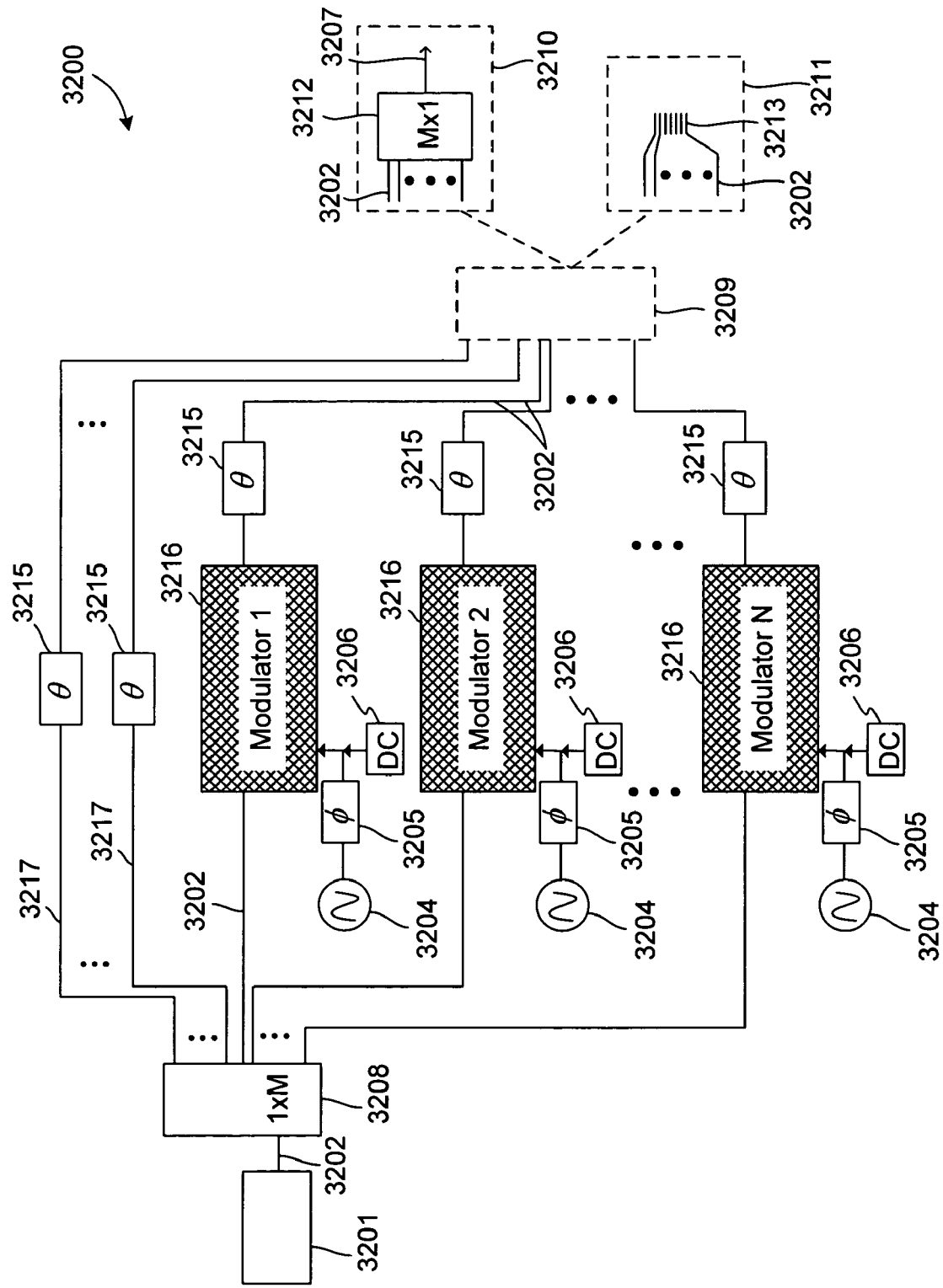
FIG. 32 is a schematic block diagram illustrating an embodiment of a high-frequency modulation structure including parallel phase modulators with mutually coherent light.

Referring to FIG. 32, a schematic block diagram illustrates an embodiment of a high-frequency modulation structure 3200 including parallel phase modulators with mutually coherent light. High frequency modulation can be attained using N parallel phase modulators as depicted. Multiple light paths are generated from a mutually coherent light beam, such as from a single source. In addition to phase modulators, additional light paths with corresponding phase delay may be added for further control of the light modulation.

Parallel phase-modulator configuration 3200 uses a mutually coherent light source. N phase modulators 3216 are used in conjunction with optical phase delay 3215. Optional phase delayed optical paths 3217 for further control of the light frequency, combining into a total of M optical paths.

The parallel phase-modulator configuration 3200 can also be implemented using bulk optics, where fiber couplers are replaced by reflective or diffractive such as grating-based beam splitters. The configuration can also be integrated on a single electro-optic chip, where light routing is achieved using optical waveguides, Y junction and/or directional coupler type beam splitters and combiners.

Output of the modulated light intensity captured by a photo-detector can be described by equation (13). Amplitude factor corresponding to loss through the optical fibers and components should be added to the equation for correct determination of the optical intensity for a particular optical system. The multiple phase modulation scheme results in higher frequency modulation than using a single modulator.

The disclosed multiple modulators can be combined with the various disclosed sensors and structures disclosed herein.

The architectures depicted in FIGS. 26, 28, and 32 generate high frequency modulated coherent light beams that are compatible with the architectures described herein throughout. In the case an expanding beam is to be used as a probe beam, cleaved fibers or waveguide components can be implemented to attain light expansion. Otherwise, refractive optical lenses can be used to attain light expansion. If a collimated laser beam is used, for example for point detection, then a negative or positive lens or diffractive optical elements can be used to collimate the beam emerging from fibers.

The incoherent scheme depicted in FIG. 30, as well as the coherent schemes depicted in FIGS. 26, 28, and 32 are suitable for generating high-frequency pump beam. Adding multiple lasers as in FIGS. 30A and 30B architectures further enhances the system by supplying a higher-power pump beam than using a single laser.

Furthermore, the cascaded and parallel schemes described herein throughout can be combined in various configurations to attain even higher modulation, and to minimize system losses and maximize performance.

The surface and subsurface detection techniques described herein can be used to check the alignment of multiple layers of a patterned wafer. The sensors described herein also can be combined with lithography tool for patterning a wafer, such as a mask aligner, to align the lithography mask to any one or multiple of surface or subsurface layers.

The sensors described herein can be mounted inside a process chamber, or access the wafer through a window inside a process chamber. In such a chamber mounted configuration, the sensor can detect formation of defects and interrogate integrity of subsurface structures, such as line edge roughness, and line slope, in real-time, or check for subsurface defects, and interrogate the integrity of subsurface structures, such as line edge roughness, and line slope, in between processing steps, without moving the sample out of the process chamber.

While the present disclosure describes various embodiments, these embodiments are to be understood as illustrative and do not limit the claim scope. Many variations, modifications, additions and improvements of the described embodiments are possible. For example, those having ordinary skill in the art will readily implement the steps necessary to provide the structures and methods disclosed herein, and will understand that the process parameters, materials, and dimensions are given by way of example only. The parameters, materials, and dimensions can be varied to achieve the desired structure as well as modifications, which are within the scope of the claims.

What is claimed is:

1. A sensor comprising:
   an optical modulator that generates a modulation signal;
   an interferometer that mixes the modulation signal with an acoustic signal evoked by a pulsed laser to down-convert the acoustic signal to lower frequencies; and
   a multiple-dimensional photodetector that detects the down-converted signal.

2. The sensor according to claim 1 further:
   a camera operative as the multiple-dimensional photodetector.

3. The sensor according to claim 1 further comprising:
   an acoustic excitation source configured to supply the acoustic signal.

4. The sensor according to claim 1 further comprising:
   the acoustic excitation source selected from a group consisting of a laser, a pulsed laser, a flash-lamp, an arc-lamp, and a thermal source.

5. The sensor according to claim 1 further comprising:
   controllable optics coupled to the interferometer and the optical modulator configured to detect surface and subsurface sample structures.

6. The sensor according to claim 1 further comprising:
   controllable optics coupled to the interferometer and the optical modulator configured to reflect elastic waves from interfaces, subsurface structures and defects in a sample; and
   a controller adapted to scan modulator frequency within a selected range, acquire measurements of a spatially-varying acoustic spectrum of the sample, and analyze the measurements for subsurface features and defects.

7. The sensor according to claim 1 further comprising:
   a continuous wave laser configured to generate laser light that is passed through the optical modulator forming a modulated continuous wave laser beam;
   the interferometer that receives and passes a pulsed laser beam and the continuous wave laser beam through a beam-splitter and an objective lens to a sample, and passes reflections from the sample back through the objective lens to the multiple-dimensional photodetector and to a reference mirror that reflects the continuous wave laser beam and sample reflections back to the multiple-dimensional photodetector; and
   processing electronics coupled to the camera and configured to perform band pass filtering, image subtraction, and image processing.

8. The sensor according to claim 1 further comprising:
   the interferometer selected from a group consisting of a Mach-Zehnder interferometer, and a Michelson interferometer.

9. The sensor according to claim 1 further comprising:
   the interferometer comprising an all-glass beam splitter/reflector interferometer including a glass block of selected length for optical delay.

10. The sensor according to claim 1 further comprising:
    the interferometer comprising a reference mirror selected from a group consisting of a planar mirror, a curved mirror with curvature configured to produce linear fringes at the multiple-dimensional photodetector, a beam-splitter, and a reference mirror positioned between an objective lens and a sample.

11. The sensor according to claim 1 further comprising:
    a diffractive or holographic optical element positioned between a pulsed laser source and the interferometer and passing a pulsed laser beam in a configuration that generates a plurality of pulsed laser spots for acoustical excitation.

12. The sensor according to claim 1 further comprising:
    a diffractive optical element, a holographic optical element, or a cylindrical lens positioned between a pulsed laser source and the interferometer and passing a pulsed laser beam in a configuration that generates a line focus.

13. The sensor according to claim 1 further comprising:
    a diffractive optical element, a holographic optical element, or a cylindrical lens positioned between a pulsed laser source and the interferometer and passing a pulsed laser beam in a configuration that produces directional sensitivity and detects anisotropy using a line focus.

14. The sensor according to claim 1 further comprising:
    the interferometer configured to produce two-dimensional data that indicates surface and subsurface structures and defects.

15. The sensor according to claim 1 further comprising:
    the optical modulator and the interferometer configured to simultaneously image multiple segments of a sample.

16. The sensor according to claim 1 further comprising:
    a 1×N fiber coupler configured to receive light from the optical modulator;
    a plurality of beam splitters coupled to receive light via the coupler;
    a plurality of objective lenses that pass light from the beam splitter plurality to a sample; and
    a plurality of photodetectors configured to receive light reflected from the sample and simultaneously acquire multiple image sample segments.

17. The sensor according to claim 1 further comprising:
    a plurality of integrated waveguide modulators configured to receive light 1 mm the optical modulator;
    a plurality of beam splitters coupled to receive light via the integrated waveguide modulator plurality;
    a plurality of objective lenses that pass light from the beam splitter plurality to a sample; and
    a plurality of photodetectors configured to receive light reflected from the sample and simultaneously acquire multiple image sample segments.

18. The sensor according to claim 1 further comprising:
    a 1×N fiber coupler configured to receive light from the optical modulator;
    a plurality of beam splitters coupled to receive light via the coupler;
    a plurality of objective lenses that pass light from the beam splitter plurality to a sample; and
    a plurality of photodetectors configured to receive light reflected from the sample and simultaneously acquire multiple image sample segments.

19. The sensor according to claim 1 further comprising:
    the sensor configuration that increases detection resolution above the interferometer optical limit.

20. The sensor according to claim 1 further comprising:
    a stepper and/or scanner configured for sub-wavelength movement of a sample or the interferometer whereby detection resolution is increased above the interferometer optical limit.

21. The sensor according to claim 1 further comprising:
    a stepper and/or scanner configured for measuring and comparing spectra from a sample segment and neighbor segments of the sample segment whereby detection resolution is increased above the interferometer optical limit.

22. The sensor according to claim 1 further comprising:
a plurality of optical fibers configured to receive light from the optical modulator and produce multiple fringe sets whereby detection resolution is increased above the interferometer optical limit.

23. The sensor according to claim 1 further comprising:
processing electronics coupled to the camera and configured to execute an acoustic spectrum analysis that measures sample critical dimensions.

24. The sensor according to claim 1 further comprising:
processing electronics coupled to the camera and configured to execute an acoustic spectrum analysis that detects line slope as a function of spectral response breadth.

25. The sensor according to claim 1 further comprising:
processing electronics coupled to the camera and configured to execute an acoustic spectrum analysis that detects an undercut line as a function of spectral shape.

26. The sensor according to claim 1 further comprising:
processing electronics coupled to the camera and configured to execute an acoustic spectrum analysis that detects line edge roughness as a function of spectral shape and spectral line broadening.

27. The sensor according to claim 1 further comprising:
processing electronics coupled to the camera and configured to execute an acoustic spectrum analysis that measures variation of thickness, slope, roughness, and undercut across a sample wafer.

28. The sensor according to claim 1 further comprising:
processing electronics coupled to the camera and configured to execute a convolution and/or correlation function to obtain shape and size of sample features.

29. The sensor according to claim 28 further comprising:
processing electronics coupled to the camera and configured to execute a Fourier transform operation that performs the correlation function in inverse spatial domain.

30. The sensor according to claim 1 further comprising:
an acoustic excitation device configured to thermally agitate electrons in a sample, the acoustic excitation device selected from a group consisting of pulsed laser, flash-lamp, arc-lamp, thermal pulse heating, and thermal excitation using thermal pulse.

31. The sensor according to claim 1 further comprising:
an acoustic excitation device configured to heat the sample, thereby increasing thermal noise that is converted to acoustic resonance.

32. The sensor according to claim 1 further comprising:
polarization optics coupled between the optical modulator and the interferometer in a configuration that improves signal-to-noise ratio and light control.

33. The sensor according to claim 1 further comprising:
polarization optics coupled between the optical modulator and the interferometer in a configuration that detects surface acoustic waves.

34. The sensor according to claim 1 further comprising:
polarization optics coupled between the optical modulator and the interferometer in a configuration that detects elastic wave induced birefringence in a sample.

35. The sensor according to claim 1 further comprising:
a controller adapted to control the sensor and check alignment of multiple layers of a patterned wafer.

36. The sensor according to claim 1 further comprising:
a lithography tool configured for patterning a wafer and aligning the lithography mask to at least one surface and/or subsurface layers.

37. The sensor according to claim 1 further comprising:
a mount configured to mount the sensor inside a process chamber or in a location enabling access to a sample through a window inside a process chamber.

38. A sensor comprising:
an optical modulator that generates a modulation signal;
an interferometer that mixes the modulation signal with an acoustic signal evoked by a pulsed laser to down-convert the acoustic signal to lower frequencies;
a photodetector that detects the down-converted signal; and
processing electronics coupled to the photodetector and configured to perform phase sensitive measurement of elastic waves.

39. The sensor according to claim 38 further comprising:
the sensor mounted to the process chamber whereby the sensor is configured to detect phenomena selected from a group consisting of defects and integrity of subsurface structures, line edge roughness, line slope, real-time phenomena in multiple processing steps while maintaining a sample in position in the process chamber.

40. The sensor according to claim 38 further comprising:
the photodetector selected from a group consisting of a camera, a two-dimensional photodetector, a single element detector, and a linear array detector.

41. The sensor according to claim 38 further comprising:
the processing electronics configured to perform a phase sensitive measurement that detects depth and location of a feature in the surface or subsurface of a sample.

42. The sensor according to claim 38 further comprising:
the processing electronics configured to perform a phase sensitive measurement that determines elastic wave path.

43. The sensor according to claim 38 further comprising:
the processing electronics configured to perform a phase sensitive measurement that increases optical resolution above the interferometer optical limit.

44. The sensor according to claim 38 further comprising:
an acoustic excitation device configured to thermally agitate electrons in a sample, the acoustic excitation device selected from a group consisting of an external pulses laser, a pulsed laser, flash-lamp, arc-lamp, thermal pulse heating, and thermal excitation using thermal pulse.

45. The sensor according to claim 38 further comprising:
a controller adapted to control the sensor and check alignment of multiple layers of a patterned wafer; and
a lithography tool configured for patterning a wafer and aligning the lithography mask to at least one surface and/Dr subsurface layers.

46. The sensor according to claim 38 further comprising:
a mount configured to mount the sensor inside a process chamber or in a location enabling access to a sample through a window inside a process chamber; and
the sensor mounted to the process chamber whereby the sensor is configured to detect phenomena selected from a group consisting of defects and integrity of subsurface structures, line edge roughness, line slope, real-time phenomena in multiple processing steps while maintaining a sample in position in the process chamber.

47. A sensor comprising:
an optical modulator that generates a modulation signal;
an interferometer that mixes the modulation signal with an acoustic signal evoked by a pump laser beam to down-convert the acoustic signal to lower frequencies;
a photodetector that detects the down-converted signal; and
a direct modulated light coupled to the interferometer and operative as an acoustic excitation source.

48. The sensor according to claim 47 further comprising:
the photodetector selected from a group consisting of a camera, a two-dimensional photodetector, a single element detector, and a linear array detector.

49. The sensor according to claim 48 further comprising:
a mount configured to mount the sensor inside a process chamber or in a location enabling access to a sample through a window inside a process chamber; and
the sensor mounted to the process chamber whereby the sensor is configured to detect phenomena selected from a group consisting of defects and integrity of subsurface structures, line edge roughness, line slope, real-time phenomena in multiple processing steps while maintaining a sample in position in the process chamber.

50. The sensor according to claim 47 further comprising:
cascaded interferometers adapted to use modulated laser beams as the acoustic excitation source.

51. The sensor according to claim 47 further comprising:
a pulsed optical modulator configured for direct light modulation as the acoustic excitation source.

52. The sensor according to claim 47 further comprising:
an acoustic excitation device configured to thermally agitate electrons in a sample, the acoustic excitation device selected from a group consisting of an acousto-optic modulator, an electro-optic modulator, an electro-absorptive modulator, a direct modulated laser, and a light modulator.

53. The sensor according to claim 47 further comprising:
a controller adapted to control the sensor and check alignment of multiple layers of a patterned wafer; and
a lithography tool configured for patterning a wafer and aligning the lithography mask to at least one surface and/or subsurface layers.

54. A sensor comprising:
an optical modulator that generates a modulation signal;
a plurality of interferometers that mix the modulation signal with an acoustic signal evoked by a pulsed laser to down-convert the acoustic signal to lower frequencies, the interferometer plurality configured to generate frequency modulation higher than attained for a singular modulator; and
a photodetector that detects the down-converted signal.

55. The sensor according to claim 54 further comprising:
the interferometer plurality are a plurality of cascaded interferometers.

56. The sensor according to claim 54 further comprising:
the interferometer plurality are a plurality of parallel amplitude modulators and a mutually coherent light source.

57. The sensor according to claim 54 further comprising:
the interferometer plurality are a plurality of parallel amplitude modulators and a plurality of mutually incoherent light sources.

58. The sensor according to claim 54 further comprising:
the interferometer plurality are a plurality of direct modulated lasers and a plurality of mutually incoherent light sources.

59. The sensor according to claim 54 further comprising:
the interferometer plurality are a plurality of parallel phase modulators and a mutually coherent light source.

60. The sensor according to claim 54 further comprising:
the interferometer plurality configured to perform acoustic excitation and detection.

61. The sensor according to claim 54 further comprising:
the photodetector selected from a group consisting of a camera, a two-dimensional photodetector, a single element detector, and a linear array detector.

* * * * *